(12) United States Patent
Kodas et al.

(10) Patent No.: US 6,360,562 B1
(45) Date of Patent: Mar. 26, 2002

(54) METHODS FOR PRODUCING GLASS POWDERS

(75) Inventors: Toivo T. Kodas; Mark J. Hampden-Smith; James Caruso; Quint H. Powell; Audunn Ludviksson, all of Albuquerque, NM (US)

(73) Assignee: Superior Micropowders LLC, Albuquerque, NM (US)

(*) Notice: Subject to any disclaimer, the term of this patent is extended or adjusted under 35 U.S.C. 154(b) by 0 days.

(21) Appl. No.: 09/141,394

(22) Filed: Aug. 27, 1998

Related U.S. Application Data

(63) Continuation-in-part of application No. 09/030,057, filed on Feb. 24, 1998, and a continuation-in-part of application No. 09/028,628, filed on Feb. 24, 1998, and a continuation-in-part of application No. 09/028,029, filed on Feb. 24, 1998, now abandoned.

(51) Int. Cl.$^7$ ............................................. C03B 19/10
(52) U.S. Cl. .................................... 65/21.1; 65/60.1
(58) Field of Search ............................... 65/17.2, 17.4, 65/21.1, 21.3, 21.4, 60.1

(56) References Cited

U.S. PATENT DOCUMENTS

| | | | |
|---|---|---|---|
| 2,935,375 A | 5/1960 | Boucher | 23/2 |
| 3,765,853 A * | 10/1973 | Riebling | 65/21.3 |
| 3,958,996 A | 5/1976 | Inskip | 96/115 |
| 4,119,480 A | 10/1978 | Nishi et al. | 156/272 |
| 4,220,582 A | 9/1980 | Orlowski et al. | 260/42.28 |
| 4,459,145 A * | 7/1984 | Elsholz | 65/21.3 |
| 4,567,030 A | 1/1986 | Yuasa et al. | 423/326 |
| 4,598,037 A | 7/1986 | Felten | 430/281 |
| 4,613,560 A | 9/1986 | Dueber et al. | 430/286 |
| 4,764,497 A | 8/1988 | Yuasa et al. | 502/235 |
| 4,775,520 A * | 10/1988 | Unger et al. | 423/335 |
| 4,820,661 A | 4/1989 | Nair | 501/79 |
| 4,871,489 A | 10/1989 | Ketcham | 264/9 |
| 4,959,330 A | 9/1990 | Donohue et al. | 501/8 |
| 5,032,478 A | 7/1991 | Nebe et al. | 430/281 |
| 5,032,490 A | 7/1991 | Nebe et al. | 430/281 |
| 5,061,682 A | 10/1991 | Aksay et al. | 505/1 |
| 5,063,179 A * | 11/1991 | Menashi et al. | 501/12 |
| 5,110,335 A * | 5/1992 | Miller et al. | 65/425 |
| 5,173,457 A | 12/1992 | Shorthouse | 501/65 |
| 5,176,732 A | 1/1993 | Block et al. | 65/21.4 |
| 5,210,057 A | 5/1993 | Haun et al. | 501/69 |
| 5,213,598 A | 5/1993 | Silingardi et al. | 65/18.1 |
| 5,236,683 A | 8/1993 | Nakazawa et al. | 423/335 |
| 5,286,269 A * | 2/1994 | Paschke et al. | 65/17.3 |
| 5,350,782 A | 9/1994 | Sasaki et al. | 523/116 |
| 5,384,306 A | 1/1995 | Konig et al. | 501/152 |
| 5,585,173 A * | 12/1996 | Kamo et al. | 428/304.4 |
| 5,609,675 A | 3/1997 | Noritake et al. | 106/35 |
| 5,622,750 A * | 4/1997 | Kilian et al. | 427/163.2 |
| 5,684,361 A | 11/1997 | Seki | 313/582 |
| 5,697,992 A | 12/1997 | Ueda et al. | 51/307 |
| 5,743,930 A * | 4/1998 | Miyake et al. | 65/142 |
| 5,849,055 A * | 12/1998 | Arai et al. | 65/17.3 |
| 5,979,185 A * | 11/1999 | Blackwell et al. | 65/17.4 |
| 6,000,241 A | 12/1999 | Ranade et al. | 65/17.2 |

\* cited by examiner

*Primary Examiner*—Sean Vincent
(74) *Attorney, Agent, or Firm*—Marsh Fischmann & Breyfogle LLP

(57) ABSTRACT

Glass powders and methods for producing glass powders. The powders preferably have a small particle size, narrow size distribution and a spherical morphology. The method includes forming the particles by a spray pyrolysis technique. The invention also includes novel devices and products formed from the glass powders.

20 Claims, 28 Drawing Sheets

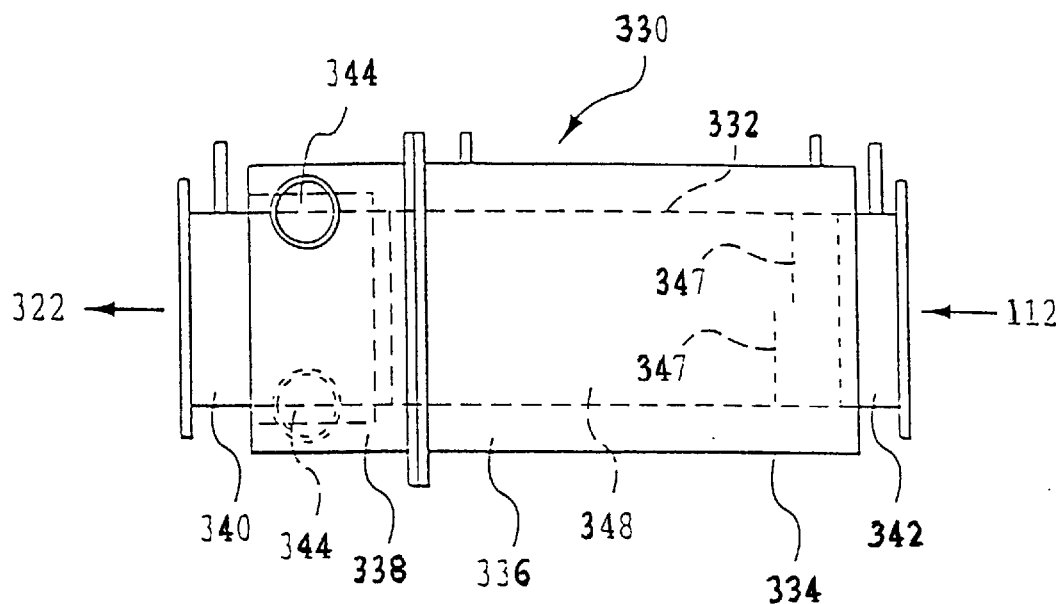
FIG. 29
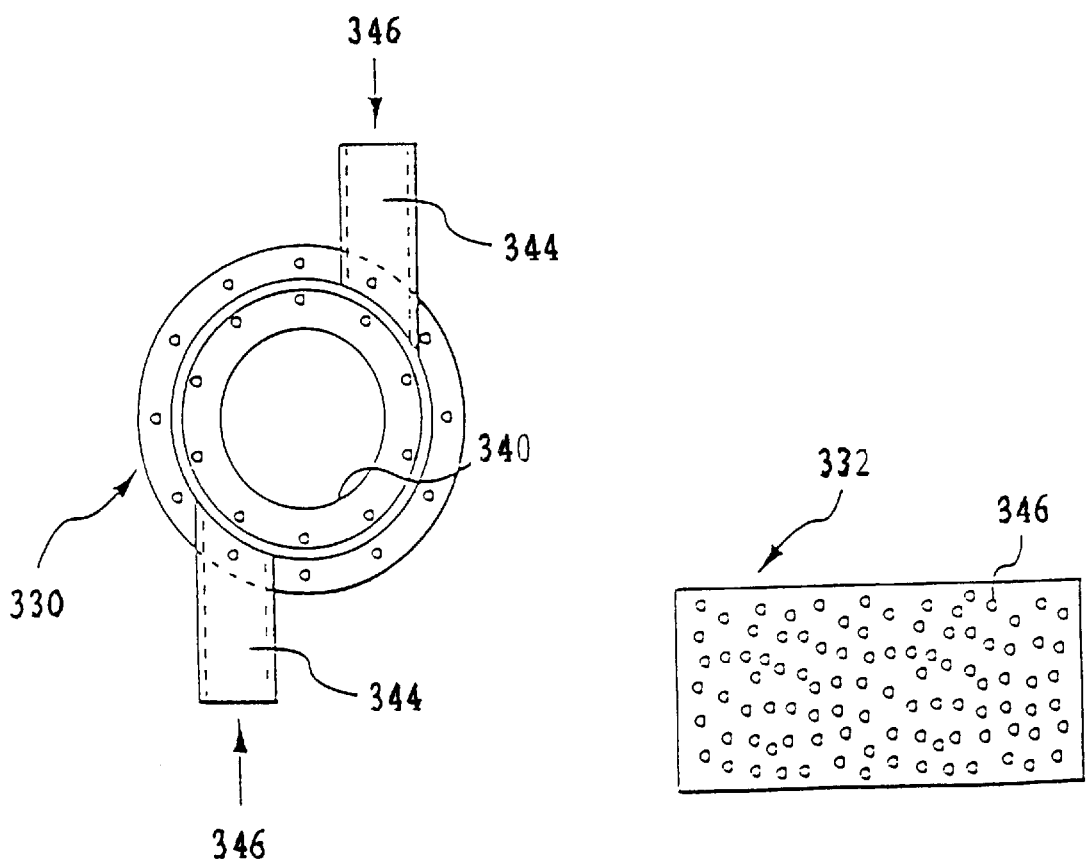
FIG. 30
FIG. 31

METHODS FOR PRODUCING GLASS POWDERS

This application is a continuation-in-part application of U.S. patent application Ser. Nos. 09/028,029 now abandoned filed Feb. 24, 1998; 09/028,628 filed Feb. 24, 1998 and 09/030,057 filed Feb. 24, 1998.

BACKGROUND OF THE INVENTION

1. Field of the Invention

The present invention relates to glass powders having well controlled chemical and mechanical properties as well as methods for producing glass powders, and intermediate products and devices incorporating the glass powders. The glass powders are preferably produced by spray pyrolysis of glass precursors.

2. Description of Related Art

Many product applications require glass powders that have one or more of the following properties: spherical morphology; high purity; small average size; narrow size distribution; controlled chemistry; and little or no agglomeration. Examples of glass powder applications requiring such characteristics include, but are not limited to, thick-film pastes used for fabricating electronic devices. Thick-film pastes are mixtures of fine powders in an organic vehicle, wherein the organic vehicle is removed after application of the paste to a substrate.

In particular, many product applications require glass powders having a small average size, such as from about 0.1 µm to about 10 µm, and a spherical morphology. It can also be advantageous if the powder consists of glass particles having a narrow size distribution without any substantial agglomeration of the particles. Most glass powders are produced by forming a melt of the desired glass composition, quenching the molten glass and milling the resulting glass to reduce the particle size of the glass. See, for example, U.S. Pat. No. 4,820,661 by Nair which discloses an aluminoborosilicate glass useful in thick-film compositions for crossover dielectrics. Such methods result in glass powders having a jagged and irregular morphology, wide spread of particle size and other characteristics which are undesirable in precision applications.

There have been attempts in the art to produce glass particles having improved chemical and physical characteristics. U.S. Pat. No. 4,775,520 by Unger et al. discloses a process for forming monodispersed silica ($SiO_2$) particles having an average size of from about 0.05 to about 10 µm. The particles, which are useful as sorption materials in chromatography, are formed by a two-step process including hydrolytic polycondensation and the addition of a silane to control the reaction.

U.S. Pat. No. 5,173,457 by Shorthouse discloses a borosilicate glass useful for thick-film applications having a size of less than 5 µm and a spherical morphology. The glass is formed by a sol-gel process.

U.S. Pat. No. 5,589,150 by Kano et al. discloses a silica gel formed by milling a hydrogel slurry and spray drying the slurry to form gel particles having an average size of 30 to 100 µm and a spherical morphology. The gel particles are useful as polymer catalyst carriers.

Typically, sol-gel and related precipitation routes for forming glasses are limited in their usefulness. The precursors, such as alkoxides, are prohibitively expensive and the process cannot easily be converted to a continuous production method. It is also difficult to produce complex glass compositions with good homogeneity of the different glass components. Further, it can be difficult to separate the glass particles from the liquid in which they are produced.

The continued miniaturization and increased complexity of electronic components has created a need for materials, including glass particles, with well-controlled physical and chemical characteristics. For example, thick-film paste technology must continue to meet the demands of decreased line width and decreased pitch, i.e., decreased distance between traces. As a result, pastes have been developed that have a photo-imaging capability to enable the formation of traces having a decreased width and pitch. In this process, a photoactive thick-film paste is applied to a substrate and the paste is then dried and exposed to ultraviolet light through a photomask and the exposed portions of the paste are developed to remove unwanted portions of the paste.

Examples of such photoactive pastes are disclosed in: U.S. Pat. No. 3,958,996 by Inskip; U.S. Pat. No. 4,119,480 by Nishi et al.; U.S. Pat. No. 4,598,037 by Felten; U.S. Pat. No. 4,613,560 by Dueber et al.; and U.S. Pat. Nos. 5,032,478 and 5,032,490 both by Nebe et al. Each of the foregoing U.S. Patents are incorporated herein by reference in their entirety.

Glass compositions for thick-film pastes are also useful for forming dielectric layers in electronic circuits. For example, U.S. Pat. No. 4,820,661 by Nair discloses an aluminoborosilcate glass useful for crossover dielectrics. U.S. Pat. No. 4,959,330 by Donohue et al. discloses a crystallizable glass including ZnO and BaO that is useful as a dielectric layer. U.S. Pat. No. 5,210,057 by Haun et al. discloses an alkaline earth zinc silicate glass that is partially crystallizable and is useful for forming dielectric layers. Each of the foregoing U.S. Patents are incorporated herein by reference in their entirety.

To meet the demands of these and similar applications, glass powders, particularly complex glass powders, having well-controlled physical and chemical characteristics are required. To date, such glass powders have not been provided.

It would be particularly advantageous to provide a flexible production method capable of producing glass powders which would enable control over the powder characteristics as well as the versatility to accommodate complex glass compositions which are either difficult or impossible to produce using existing production methods. For example, it would be advantageous to provide control over the particle size, particle size distribution, morphology, homogeneity, and porosity of the glass powder. It would be particularly advantageous if such glass powders could be produced in large quantities on a substantially continuous basis.

FIG. 15 is a top view of one embodiment of a gas distribution plate/gas tube assembly of the aerosol generator of the present invention.

FIG. 16 is a side view of one embodiment of the gas distribution plate/gas tube assembly shown in FIG. 15.

FIG. 17 shows one embodiment for orienting a transducer in the aerosol generator of the present invention.

FIG. 18 is a top view of a gas manifold for distributing gas within an aerosol generator of the present invention.

FIG. 19 is a side view of the gas manifold shown in FIG. 18.

FIG. 20 is a top view of a generator lid of a hood design for use in an aerosol generator of the present invention.

FIG. 21 is a side view of the generator lid shown in FIG. 20.

FIG. 22 is a process block diagram of one embodiment of the process of the present invention including a droplet classifier.

FIG. 23 is a top view in cross section of an impactor of the present invention for use in classifying an aerosol.

FIG. 24 is a front view of a flow control plate of the impactor shown in FIG. 23.

FIG. 25 is a front view of a mounting plate of the impactor shown in FIG. 23.

FIG. 26 is a front view of an impactor plate assembly of the impactor shown in FIG. 23.

FIG. 27 is a side view of the impactor plate assembly shown in FIG. 26.

FIG. 28 is a process block diagram of one embodiment of the present invention including a particle cooler.

FIG. 29 is a top view of a gas quench cooler of the present invention.

FIG. 30 is an end view of the gas quench cooler shown in FIG. 29.

FIG. 31 is a side view of a perforated conduit of the quench cooler shown in FIG. 29.

FIG. 32 is a side view showing one embodiment of a gas quench cooler of the present invention connected with a cyclone.

FIG. 33 is a process block diagram of one embodiment of the present invention including a particle coater.

FIG. 34 is a block diagram of one embodiment of the present invention including a particle modifier.

FIG. 35 shows cross sections of various particle morphologies of some composite particles manufacturable according to the present invention.

FIG. 36 is a block diagram of one embodiment of the process of the present invention including the addition of a dry gas between the aerosol generator and the furnace.

FIG. 37 illustrates an SEM photomicrograph of a glass powder produced according to an embodiment of the present invention.

FIG. 38 illustrates a particle size distribution for a glass powder batch according to an embodiment of the present invention.

DETAILED DESCRIPTION OF THE INVENTION

The present invention is generally directed to glass powders and methods for producing glass powders. The invention is also directed to novel intermediate products and devices fabricated using the glass powders. As used herein, glass powders or glass particles are inorganic materials that are predominately amorphous, as determined, for example, by x-ray diffraction analysis of the powder. Glasses are characterized by a random structure with no long-range (crystalline) order. Finely powdered glass powders are sometimes referred to as glass frits or fillers.

The present invention is particularly applicable to complex glasses. As used herein, complex glasses are those that include at least one structural forming oxide (e.g. $SiO_2$) and at least one additional oxide (e.g. $B_2O_3$, PbO). Complex glasses include binary, ternary or quaternary glasses, as well as glasses including more than four components. Examples of particularly preferred complex glasses are disclosed in detail hereinbelow.

In one aspect, the present invention provides a method for preparing a particulate product including a glass. A feed of liquid-containing, flowable medium, including at least one precursor for the desired glass material, is converted to aerosol form, with droplets of the medium being dispersed in and suspended by a carrier gas. Liquid from the droplets in the aerosol is then removed to permit formation in a dispersed state of the desired particles. Typically, the feed precursor is pyrolyzed in a furnace to make the particles. In one embodiment, the particles are subjected, while still in a dispersed state, to compositional or structural modification, if desired. Compositional modification may include, for example, coating the particles. Structural modification may include, for example, annealing the particles. The term powder is often used herein to refer to the particulate product of the present invention. The use of the term powder does not indicate, however, that the particulate product must be dry or in any particular environment. Although the particulate product is typically manufactured in a dry state, the particulate product may, after manufacture, be placed in a wet environment, such as in a paste or slurry.

The process of the present invention is particularly well suited for the production of finely divided glass particles having a small weight average size. In addition to making particles within a small weight average particle size, the particles may be produced with a narrow size distribution, thereby providing size uniformity that is desired for many applications.

In addition to control over particle size and size distribution, the method of the present invention provides significant flexibility for producing particles of varying chemical composition wherein the particles are high purity with good chemical homogeneity. Complex glasses, such as binary, ternary or quaternary glasses, can be formed by the method. The ability to tightly control the chemical composition of the glass particles advantageously permits control over the properties of the glass such as glass transition temperature ($T_g$), dielectric constant, density, and the like.

The glass particles may also include a second-phase that is not a glass. For example, one phase (e.g. a crystalline oxide) may be uniformly dispersed throughout a matrix of another phase (e.g. a glass). Alternatively, one phase may form an interior core while another phase forms a coating that surrounds the core. Other morphologies are also possible, as is discussed more fully below.

Figure 1:
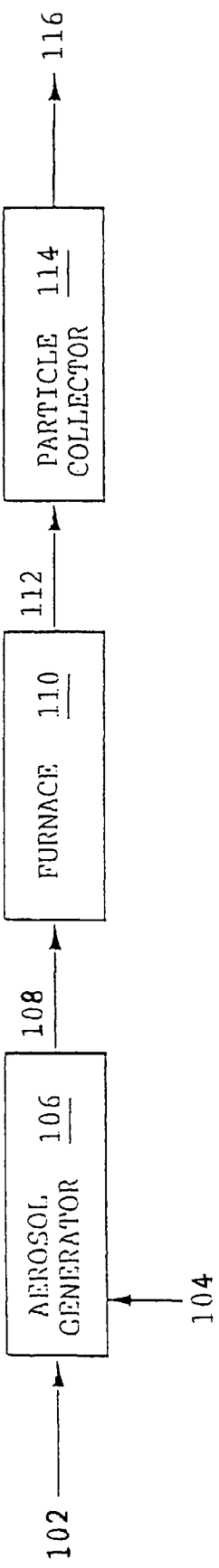
FIG. 1 is a process block diagram showing one embodiment of the process of the present invention.

Referring now to FIG. 1, one embodiment of the process of the present invention is described. A liquid feed 102, including at least one precursor for the desired particles, and a carrier gas 104 are fed to an aerosol generator 106 where an aerosol 108 is produced. The aerosol 108 is then fed to a furnace 110 where liquid in the aerosol 108 is removed to produce glass particles 112 that are dispersed in and suspended by gas exiting the furnace 110. The glass particles 112 are then collected in a particle collector 114 to produce a particulate product 116.

As used herein, the liquid feed 102 is a feed that includes one or more flowable liquids as the major constituent(s), such that the feed is a flowable medium. The liquid feed 102 need not comprise only liquid constituents. The liquid feed 102 may comprise only constituents in one or more liquid phase, or it may also include particulate material suspended in a liquid phase. The liquid feed 102 must, however, be capable of being atomized to form droplets of sufficiently small size for preparation of the aerosol 108. Therefore, if the liquid feed 102 includes suspended particles, such as colloidal silica particles, those particles should be relatively small in relation to the size of droplets in the aerosol 108. Such suspended particles should typically be smaller than about 1 $\mu$m in size, preferably smaller than about 0.5 $\mu$m in size, and more preferably smaller than about 0.3 $\mu$m in size and most preferably smaller than about 0.1 $\mu$m in size. Most preferably, the suspended particles should be able to form a colloid. The suspended particles could be finely divided particles, or could be agglomerate masses comprised of agglomerated smaller primary particles. For example, 0.5 $\mu$m particles could be agglomerates of nanometer-sized primary particles. When the liquid feed 102 includes suspended particles, the particles preferably comprise not greater than about 15 weight percent of the liquid feed.

As noted, the liquid feed 102 includes at least one precursor for preparation of the particles 112. The precursor may be a substance in either a liquid or solid phase of the liquid feed 102. Preferably, the precursor will be a material dissolved in a liquid solvent of the liquid feed 102, such as a salt, e.g., a nitrate salt. The precursor can also be an acid, such as boric acid ($H_3BO_3$), a precursor to $B_2O_3$. The precursor may undergo one or more chemical reactions in the furnace 110 to assist in production of the particles 112. Alternatively, the precursor material may contribute to formation of the particles 112 without undergoing chemical reaction. This could be the case, for example, when the liquid feed 102 includes, as a precursor material, suspended particles that are not chemically modified in the furnace 110. In any event, the particles 112 comprise at least one component originally contributed by the precursor.

For the production of complex glass powders, the liquid feed 102 will typically include multiple precursor materials, which may be present together in a single phase or separately in multiple phases. For example, the liquid feed 102 may include multiple precursors in solution in a single liquid vehicle. Alternatively, one precursor material could be in a solid particulate phase (e.g. colloidal silica) and a second precursor material could be in a liquid phase (e.g. a metal salt). Also, one precursor material could be in one liquid phase and a second precursor material could be in a second liquid phase, such as could be the case when the liquid feed 102 comprises an emulsion. One of the advantages of the present invention is that high quality glass powders can be produced from reasonably inexpensive precursor materials.

The carrier gas 104 may comprise any gaseous medium in which droplets produced from the liquid feed 102 may be dispersed in aerosol form. The carrier gas 104 may be inert, in that the carrier gas 104 does not participate in formation of the particles 112. Alternatively, the carrier gas may have one or more active component(s) that contribute to formation of the particles 112. In that regard, the carrier gas may include one or more reactive components that react in the furnace 110 to contribute to formation of the glass particles 112. For example, oxygen can be a critical reactive component to the formation of the glass particles.

The aerosol generator 106 atomizes the liquid feed 102 to form droplets in a manner to permit the carrier gas 104 to sweep the droplets away to form the aerosol 108. The droplets comprise liquid from the liquid feed 102. The droplets may also include nonliquid material, such as one or more small particles held in the droplet by the liquid. For example, when producing glass composite particles, one phase of the particles may be provided in the liquid feed 102 in the form of suspended precursor particles and a second phase of the particles may be produced in the furnace 110 from one or more precursors in the liquid phase of the liquid feed 102. Furthermore the precursor particles could be included in the liquid feed 102, and therefore also in droplets of the aerosol 108, for the purpose only of dispersing the particles for subsequent compositional or structural modification during or after processing in the furnace 110.

An important aspect of the present invention is generation of the aerosol 108 with droplets of a small average size and narrow size distribution. In this manner, the glass particles 112 may be produced at a desired small size with a narrow size distribution, which are advantageous for many applications.

The aerosol generator 106 is preferably capable of producing the aerosol 108 such that it includes droplets having a weight average size in a range having a lower limit of about 1 $\mu$m and preferably about 2 $\mu$m; and an upper limit of about 20 $\mu$m; preferably about 10 $\mu$m, more preferably about 7 $\mu$m and most preferably about 5 $\mu$m. A weight average droplet size in a range of from about 2 $\mu$m to about 4 $\mu$m is preferred for many applications. The aerosol generator is also preferably capable of producing the aerosol 108 such that it includes droplets in a narrow size distribution. Preferably, the droplets in the aerosol are such that at least about 70 weight percent (more preferably at least about 80 weight percent and most preferably at least about 85 weight percent) of the droplets are smaller than about 10 $\mu$m and more preferably at least about 70 weight percent (more preferably at least about 80 weight percent and most preferably at least about 85 weight percent) are smaller than about 5 $\mu$m. Furthermore, preferably no greater than about 30 weight percent, more preferably no greater than about 25 weight percent and most preferably no greater than about 20 weight percent, of the droplets in the aerosol 108 are larger than about twice the weight average droplet size.

Another important aspect of the present invention is that the aerosol 108 may be generated without consuming excessive amounts of the carrier gas 104. The aerosol generator 106 is capable of producing the aerosol 108 such that it has a high loading, or high concentration, of the liquid feed 102 in droplet form. In that regard, the aerosol 108 preferably includes greater than about $1 \times 10^6$ droplets per cubic centimeter of the aerosol 108, more preferably greater than about $5 \times 10^6$ droplets per cubic centimeter, still more preferably greater than about $1 \times 10^7$ droplets per cubic centimeter, and most preferably greater than about $5 \times 10^7$ droplets per cubic centimeter. That the aerosol generator 106 can produce such a heavily loaded aerosol 108 is particularly surprising considering the high quality of the aerosol 108 with respect to small average droplet size and narrow droplet size distribution. Typically, droplet loading in the aerosol is such that the volumetric ratio of liquid feed 102 to carrier gas 104 in the aerosol 108 is larger than about 0.04 milliliters of liquid feed 102 per liter of carrier gas 104 in the aerosol 108, preferably larger than about 0.083 milliliters of liquid feed 102 per liter of carrier gas 104 in the aerosol 108, more preferably larger than about 0.167 milliliters of liquid feed 102 per liter of carrier gas 104, still more preferably larger than about 0.25 milliliters of liquid feed 102 per liter of carrier gas 104, and most preferably larger than about 0.333 milliliters of liquid feed 102 per liter of carrier gas 104.

This capability of the aerosol generator 106 to produce a heavily loaded aerosol 108 is even more surprising given the high droplet output rate of which the aerosol generator 106 is capable, as discussed more fully below. It will be appreciated that the concentration of liquid feed 102 in the aerosol 108 will depend upon the specific components and attributes of the liquid feed 102 and, particularly, the size of the droplets in the aerosol 108. For example, when the average droplet size is from about 2 $\mu$m to about 4 $\mu$m, the droplet loading is preferably larger than about 0.15 milliliters of aerosol feed 102 per liter of carrier gas 104, more preferably larger than about 0.2 milliliters of liquid feed 102 per liter of carrier gas 104, even more preferably larger than about 0.25 milliliters of liquid feed 102 per liter of carrier gas 104, and most preferably larger than about 0.3 milliliters of liquid feed 102 per liter of carrier gas 104. When reference is made herein to liters of carrier gas 104, it refers to the volume that the carrier gas 104 would occupy under conditions of standard temperature and pressure.

The furnace 110 may be any suitable device for heating the aerosol 108 to evaporate liquid from the droplets of the aerosol 108 and thereby permit formation of the glass particles 112. The maximum average stream temperature, or reaction temperature, refers to the maximum average temperature that an aerosol stream attains while flowing through the furnace. This is typically determined by a temperature probe inserted into the furnace.

For the production of glass particles, residence time in the heating zone of the furnace 110 will depend on the composition of the glass particles. In one embodiment, the residence time in the heating zone is at least about 4 seconds, with shorter than about 15 seconds being preferred. The residence time will depend on the reaction temperature as well as the geometric size of the reactor and the carrier gas flow rate. The residence time should be long enough, however, to assure that the particles 112 attain the desired maximum stream temperature for a given heat transfer rate such that substantially all of the precursors are fully reacted. In that regard, with extremely short residence times, higher furnace temperatures could be used to increase the rate of heat transfer so long as the particles 112 attain a maximum temperature within the desired stream temperature range. However, the temperature should not be so high that volatile species (e.g. PbO) are lost. Thus, that mode of operation is not typically preferred. Also, it is preferred that, in most cases, the maximum stream temperature not be attained in the furnace 110 until substantially at the end of the heating zone in the furnace 110. For example, the heating zone will often include a plurality of heating sections that are each independently controllable. The maximum stream temperature should typically not be attained until the final heating section, and more preferably until substantially at the end of the last heating section. This is important to reduce the potential for thermophoretic losses of material. Also, it is noted that as used herein, residence time refers to the actual time for a material to pass through the relevant process equipment. In the case of the furnace, this includes the effect of increasing velocity with gas expansion due to heating.

Typically, the furnace 110 will be a tube-shaped furnace, so that the aerosol 108 moving into and through the furnace does not encounter sharp edges on which droplets could collect. Loss of droplets to collection at sharp surfaces results in a lower yield of particles 112. Further, the accumulation of liquid at sharp edges can result in re-release of undesirably large droplets back into the aerosol 108, which can cause contamination of the particulate product 116 with undesirably large particles. Also, over time, such liquid collection at sharp surfaces can cause fouling of process equipment, impairing process performance.

The furnace 110 may include a heating tube made of any suitable material. The tube material may be a ceramic material, for example, mullite, fused silica or alumina. Alternatively, the tube may be metallic. Advantages of using a metallic tube are low cost, ability to withstand steep temperature gradients and large thermal shocks, machinability and weldability, and ease of providing a seal between the tube and other process equipment. Disadvantages of using a metallic tube include limited operating temperature and increased reactivity in some reaction systems. For example, some metal tubes can out-gas chromium at increased temperatures and very small amounts of chromium (e.g. as little as 150 ppm) can discolor the glass particles. Given the foregoing, the proper tube can be selected for a particular glass composition and reactor temperature. For making high purity glass particles, fused silica (quartz) tubes are often preferred.

When a metallic tube is used in the furnace 110, it is preferably a high nickel content stainless steel alloy, such as a 330 stainless steel, or a nickel-based super alloy. As noted, one of the major advantages of using a metallic tube is that the tube is relatively easy to seal with other process equipment. In that regard, flange fittings may be welded directly to the tube for connecting with other process equipment. Metallic tubes are generally preferred for making particles that do not require a maximum tube wall temperature of higher than about 1100° C. during particle manufacture. When higher temperatures are required, ceramic tubes are typically used. One major problem with ceramic tubes, however, is that the tubes can be difficult to seal with other process equipment, especially when the ends of the tubes are maintained at relatively high temperatures.

Also, although the present invention is described with primary reference to a furnace reactor, which is preferred, it should be recognized that, except as noted, any other thermal reactor, including a flame reactor or a plasma reactor, could be used instead. A furnace reactor is, however, preferred, because of the generally even heating characteristic of a furnace for attaining a uniform stream temperature.

The particle collector 114, may be any suitable apparatus for collecting glass particles 112 to produce the particulate product 116. One embodiment of the particle collector 114 uses one or more filters to separate the glass particles 112 from the gas. Such a filter may be of any type, including a bag filter. Another preferred embodiment of the particle collector uses one or more cyclones to separate the particles 112. A cyclone is preferred according to one embodiment of the present invention due to the ability of a cyclone to separate the glass powder based upon particle size. Thus, the collected particles can advantageously have an even narrower particle size distribution. Other apparatus that may be used in the particle collector 114 include an electrostatic precipitator. Collection should normally occur at a temperature above the condensation temperature of the gas stream in which the glass particles 112 are suspended. Also, collection should normally be at a temperature that is low enough to prevent significant agglomeration of the glass particles 112, that is, the temperature should be below the softening point of the glass.

Figure 2:
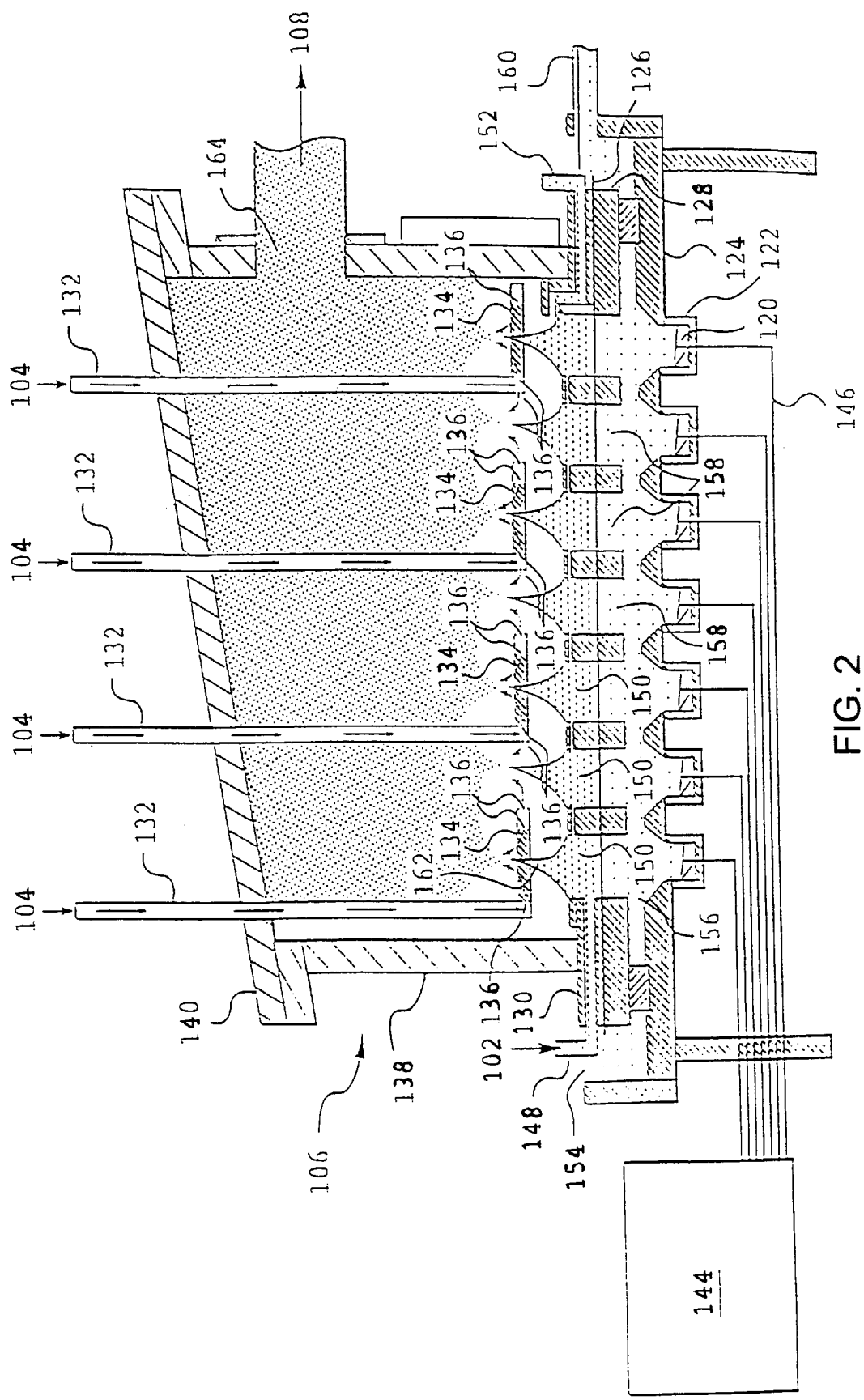
FIG. 2 is a side view in cross section of one embodiment of aerosol generator of the present invention.
Figure 3:
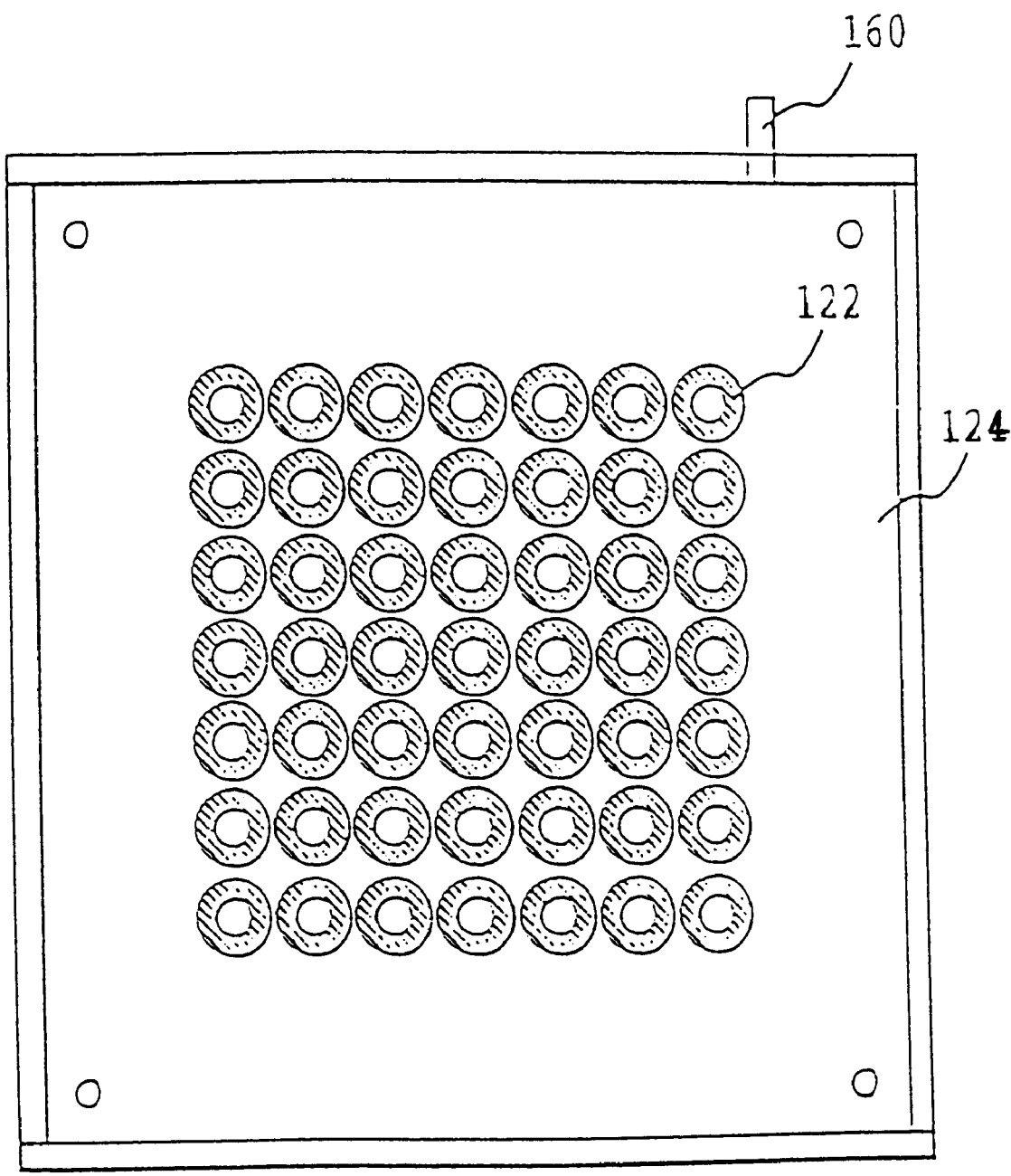
FIG. 3 is a top view of a transducer mounting plate showing a 49 transducer array or use in an aerosol generator of the present invention.

Of significant importance to the operation of the process of the present invention is the aerosol generator 106, which must be capable of producing a high quality aerosol with high droplet loading, as previously noted. With reference to FIG. 2, one embodiment of an aerosol generator 106 of the present invention is described. The aerosol generator 106 includes a plurality of ultrasonic transducer discs 120 that are each mounted in a transducer housing 122. The transducer housings 122 are mounted to a transducer mounting plate 124, creating an array of the ultrasonic transducer discs 120. Any convenient spacing may be used for the ultrasonic transducer discs 120. Center-to-center spacing of the ultrasonic transducer discs 120 of about 4 centimeters is often adequate. The aerosol generator 106, as shown in FIG. 2, includes forty-nine transducers in a 7×7 array. The array configuration is as shown in FIG. 3, which depicts the locations of the transducer housings 122 mounted to the transducer mounting plate 124.

With continued reference to FIG. 2, a separator 126, in spaced relation to the transducer discs 120, is retained between a bottom retaining plate 128 and a top retaining plate 130. Gas delivery tubes 132 are connected to gas distribution manifolds 134, which have gas delivery ports 136. The gas distribution manifolds 134 are housed within a generator body 138 that is covered by generator lid 140. A transducer driver 144, having circuitry for driving the transducer discs 120, is electronically connected with the transducer discs 120 via electrical cables 146.

During operation of the aerosol generator 106, as shown in FIG. 2, the transducer discs 120 are activated by the transducer driver 144 via the electrical cables 146. The transducers preferably vibrate at a frequency of from about 1 MHz to about 5 MHz, more preferably from about 1.5 MHz to about 3 MHz. Frequently used frequencies are at about 1.6 MHz and about 2.4 MHz. Furthermore, all of the transducer discs 110 should be operating at substantially the same frequency when an aerosol with a narrow droplet size distribution is desired. This is important because commercially available transducers can vary significantly in thickness, sometimes by as much as 10%. It is preferred, however, that the transducer discs 120 operate at frequencies within a range of 5% above and below the median transducer frequency, more preferably within a range of 2.5%, and most preferably within a range of 1%. This can be accomplished by careful selection of the transducer discs 120 so that they all preferably have thicknesses within 5% of the median transducer thickness, more preferably within 2.5%, and most preferably within 1%.

Liquid feed 102 enters through a feed inlet 148 and flows through flow channels 150 to exit through feed outlet 152. An ultrasonically transmissive fluid, typically water, enters through a water inlet 154 to fill a water bath volume 156 and flow through flow channels 158 to exit through a water outlet 160. A proper flow rate of the ultrasonically transmissive fluid is necessary to cool the transducer discs 120 and to prevent overheating of the ultrasonically transmissive fluid. Ultrasonic signals from the transducer discs 120 are transmitted, via the ultrasonically transmissive fluid, across the water bath volume 156, and ultimately across the separator 126, to the liquid feed 102 in flow channels 150.

The ultrasonic signals from the ultrasonic transducer discs 120 cause atomization cones 162 to develop in the liquid feed 102 at locations corresponding with the transducer discs 120. Carrier gas 104 is introduced into the gas delivery tubes 132 and delivered to the vicinity of the atomization cones 162 via gas delivery ports 136. Jets of carrier gas exit the gas delivery ports 136 in a direction so as to impinge on the atomization cones 162, thereby sweeping away atomized droplets of the liquid feed 102 that are being generated from the atomization cones 162 and creating the aerosol 108, which exits the aerosol generator 106 through an aerosol exit opening 164.

Efficient use of the carrier gas 104 is an important aspect of the aerosol generator 106. The embodiment of the aerosol generator 106 shown in FIG. 2 includes two gas exit ports per atomization cone 162, with the gas ports being positioned above the liquid medium 102 over troughs that develop between the atomization cones 162, such that the exiting carrier gas 104 is horizontally directed at the surface of the atomization cones 162, thereby efficiently distributing the carrier gas 104 to critical portions of the liquid feed 102 for effective and efficient sweeping away of droplets as they form about the ultrasonically energized atomization cones 162. Furthermore, it is preferred that at least a portion of the opening of each of the gas delivery ports 136, through which the carrier gas exits the gas delivery tubes, should be located below the top of the atomization cones 162 at which the carrier gas 104 is directed. This relative placement of the gas delivery ports 136 is very important to efficient use of carrier gas 104. Orientation of the gas delivery ports 136 is also important. Preferably, the gas delivery ports 136 are positioned to horizontally direct jets of the carrier gas 104 at the atomization cones 162. The aerosol generator 106 permits generation of the aerosol 108 with heavy loading with droplets of the carrier liquid 102, unlike aerosol generator designs that do not efficiently focus gas delivery to the locations of droplet formation.

Another important feature of the aerosol generator 106, as shown in FIG. 2, is the use of the separator 126, which protects the transducer discs 120 from direct contact with the liquid feed 102, which is often highly corrosive. The height of the separator 126 above the top of the transducer discs 120 should normally be kept as small as possible, and is often in the range of from about 1 centimeter to about 2 centimeters. The top of the liquid feed 102 in the flow channels above the tops of the ultrasonic transducer discs 120 is typically in a range of from about 2 centimeters to about 5 centimeters, whether or not the aerosol generator includes the separator 126, with a distance of about 3 to 4 centimeters being preferred. Although the aerosol generator 106 could be made without the separator 126, in which case the liquid feed 102 would be in direct contact with the transducer discs 120, the highly corrosive nature of the liquid feed 102 can often cause premature failure of the transducer discs 120. The use of the separator 126, in combination with use of the ultrasonically transmissive fluid in the water bath volume 156 to provide ultrasonic coupling, significantly extends the life of the ultrasonic transducers 120. One disadvantage of using the separator 126, however, is that the rate of droplet production from the atomization cones 162 is reduced, often by a factor of two or more, relative to designs in which the liquid feed 102 is in direct contact with the ultrasonic transducer discs 102. Even with the separator 126, however, the aerosol generator 106 used with the present invention is capable of producing a high quality aerosol with heavy droplet loading, as previously discussed. Suitable materials for the separator 126 include, for example, polyamides (such as Kapton™ membranes from DuPont) and other polymer materials, glass, and plexiglass. The main requirements for the separator 126 are that it be ultrasonically transmissive, corrosion resistant and impermeable.

One alternative to using the separator 126 is to bind a corrosion-resistant protective coating onto the surface of the ultrasonic transducer discs 120, thereby preventing the liquid feed 102 from contacting the surface of the ultrasonic transducer discs 120. When the ultrasonic transducer discs 120 have a protective coating, the aerosol generator 106 will typically be constructed without the water bath volume 156 and the liquid feed 102 will flow directly over the ultrasonic transducer discs 120. Examples of such protective coating materials include platinum, gold, TEFLON™, epoxies and various plastics. Such a coating can significantly extend the transducer life. Also, when operating without the separator 126, the aerosol generator 106 will typically produce the aerosol 108 with a much higher droplet loading than when the separator 126 is used.

One surprising finding with operation of the aerosol generator 106 of the present invention is that the droplet loading in the aerosol may be affected by the temperature of the liquid feed 102. It has been found that when the liquid feed 102 includes an aqueous liquid at an elevated temperature, the droplet loading increases significantly. The temperature of the liquid feed 102 is preferably higher than about 30° C., more preferably higher than about 35° C. and most preferably higher than about 40° C. If the temperature becomes too high, however, it can have a detrimental effect on droplet loading in the aerosol 108. Therefore, the temperature of the liquid feed 102 from which the aerosol 108 is made should generally be lower than about 50° C., and preferably lower than about 45° C. The liquid feed 102 may be maintained at the desired temperature in any suitable fashion. For example, the portion of the aerosol generator 106 where the liquid feed 102 is converted to the aerosol 108 could be maintained at a constant elevated temperature. Alternatively, the liquid feed 102 could be delivered to the aerosol generator 106 from a constant temperature bath maintained separate from the aerosol generator 106. When the ultrasonic generator 106 includes the separator 126, the ultrasonically transmissive fluid adjacent the ultrasonic transducer discs 120 are preferably also at an elevated temperature in the ranges discussed for the liquid feed 102.

The design for the aerosol generator 106 based on an array of ultrasonic transducers is versatile and is easily modified to accommodate different generator sizes for different specialty applications. The aerosol generator 106 may be designed to include a plurality of ultrasonic transducers in any convenient number. Even for smaller scale production, however, the aerosol generator 106 preferably has at least nine ultrasonic transducers, more preferably at least 16 ultrasonic transducers, and even more preferably at least 25 ultrasonic transducers. For larger scale production, however, the aerosol generator 106 includes at least 40 ultrasonic transducers, more preferably at least 100 ultrasonic transducers, and even more preferably at least 400 ultrasonic transducers. In some large volume applications, the aerosol generator may have at least 1000 ultrasonic transducers.

Figure 4:
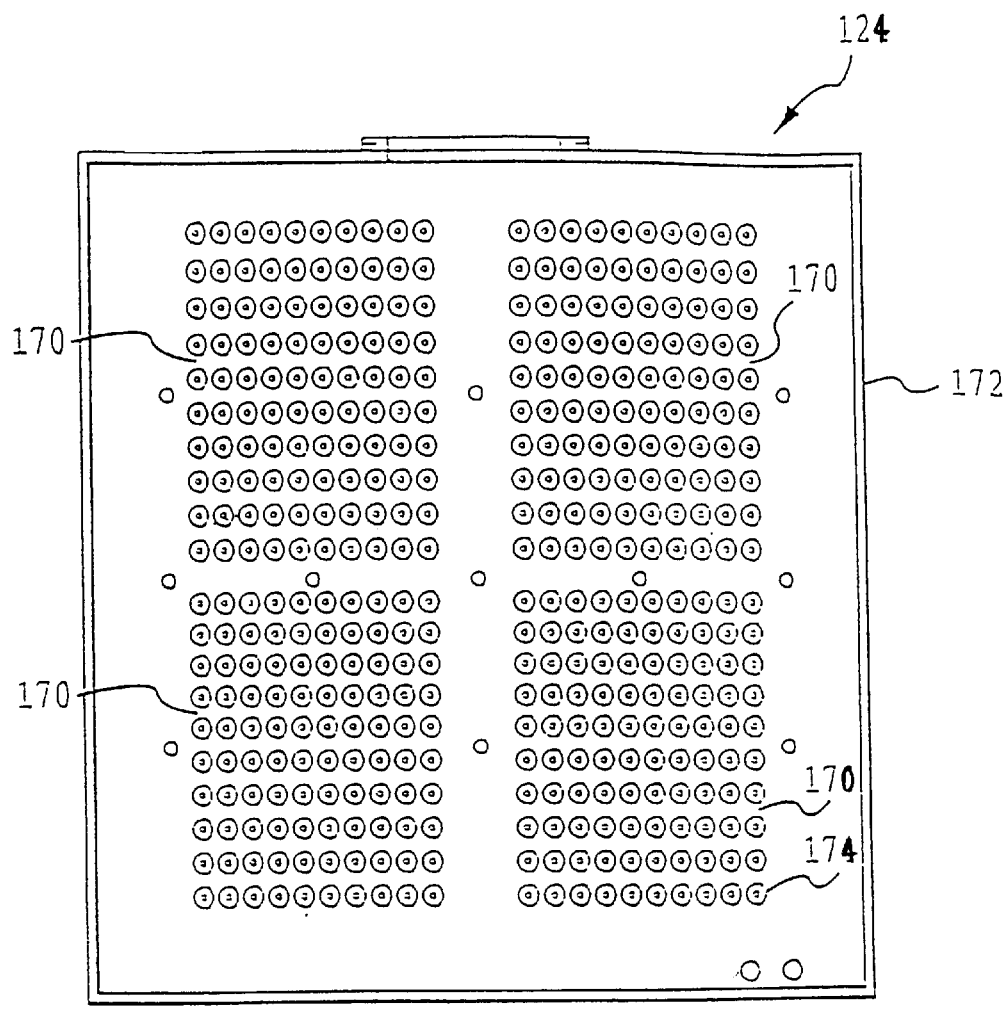
FIG. 4 is a top view of a transducer mounting plate for a 400 transducer array for use in an ultrasonic generator of the present invention.
Figure 5:
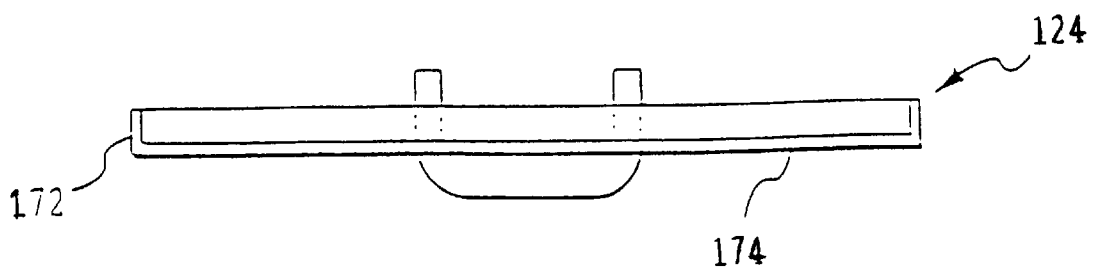
FIG. 5 is a side view of the transducer mounting plate shown in FIG. 4.

FIGS. 4–21 show component designs for an aerosol generator 106 including an array of 400 ultrasonic transducers. Referring first to FIGS. 4 and 5, the transducer mounting plate 124 is shown with a design to accommodate an array of 400 ultrasonic transducers, arranged in four subarrays of 100 ultrasonic transducers each. The transducer mounting plate 124 has integral vertical walls 172 for containing the ultrasonically transmissive fluid, typically water, in a water bath similar to the water bath volume 156 described previously with reference to FIG. 2.

Figure 6:
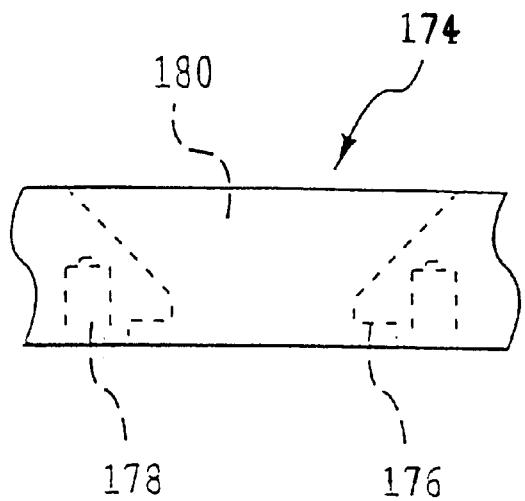
FIG. 6 is a partial side view showing the profile of a single transducer mounting receptacle of the transducer mounting plate shown in FIG. 4.

As shown in FIGS. 4 and 5, four hundred transducer mounting receptacles 174 are provided in the transducer mounting plate 124 for mounting ultrasonic transducers for the desired array. With reference to FIG. 6, the profile of an individual transducer mounting receptacle 174 is shown. A mounting seat 176 accepts an ultrasonic transducer for mounting, with a mounted ultrasonic transducer being held in place via screw holes 178. Opposite the mounting receptacle 176 is a flared opening 180 through which an ultrasonic signal may be transmitted for the purpose of generating the aerosol 108, as previously described with reference to FIG. 2.

Figure 7:
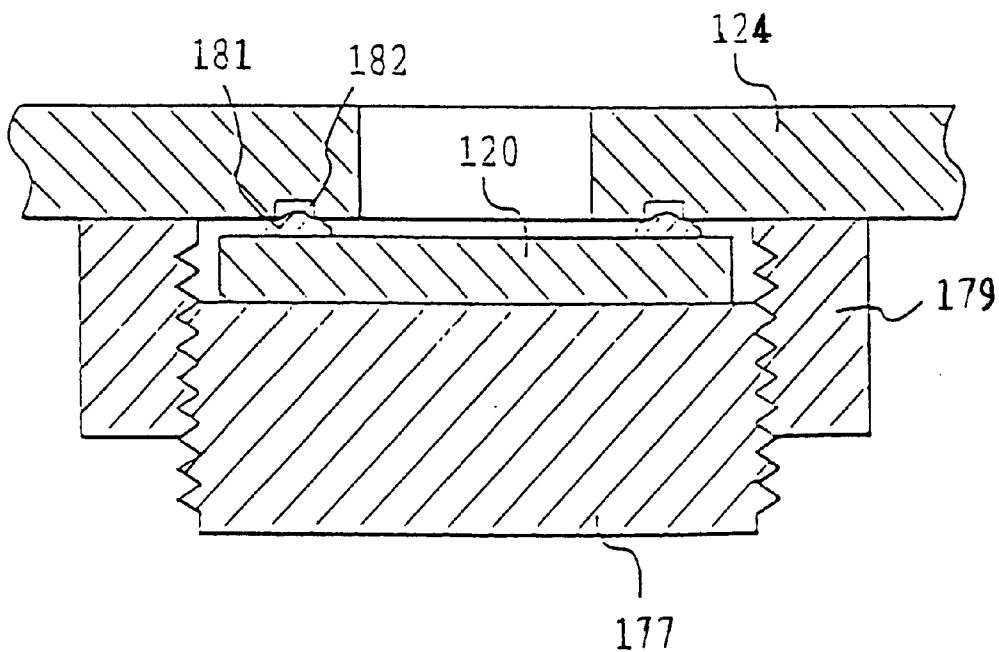
FIG. 7 is a partial side view in cross-section showing an alternative embodiment for mounting an ultrasonic transducer.

A preferred transducer mounting configuration, however, is shown in FIG. 7 for another configuration for the transducer mounting plate 124. As illustrated in FIG. 7, an ultrasonic transducer disc 120 is mounted to the transducer mounting plate 124 by use of a compression screw 177 threaded into a threaded receptacle 179. The compression screw 177 bears against the ultrasonic transducer disc 120, causing an o-ring 181, situated in an o-ring seat 182 on the transducer mounting plate, to be compressed to form a seal between the transducer mounting plate 124 and the ultrasonic transducer disc 120. This type of transducer mounting is particularly preferred when the ultrasonic transducer disc 120 includes a protective surface coating, as discussed previously, because the seal of the o-ring to the ultrasonic transducer disc 120 will be inside of the outer edge of the protective seal, thereby preventing liquid from penetrating under the protective surface coating from the edges of the ultrasonic transducer disc 120.

Figure 8:
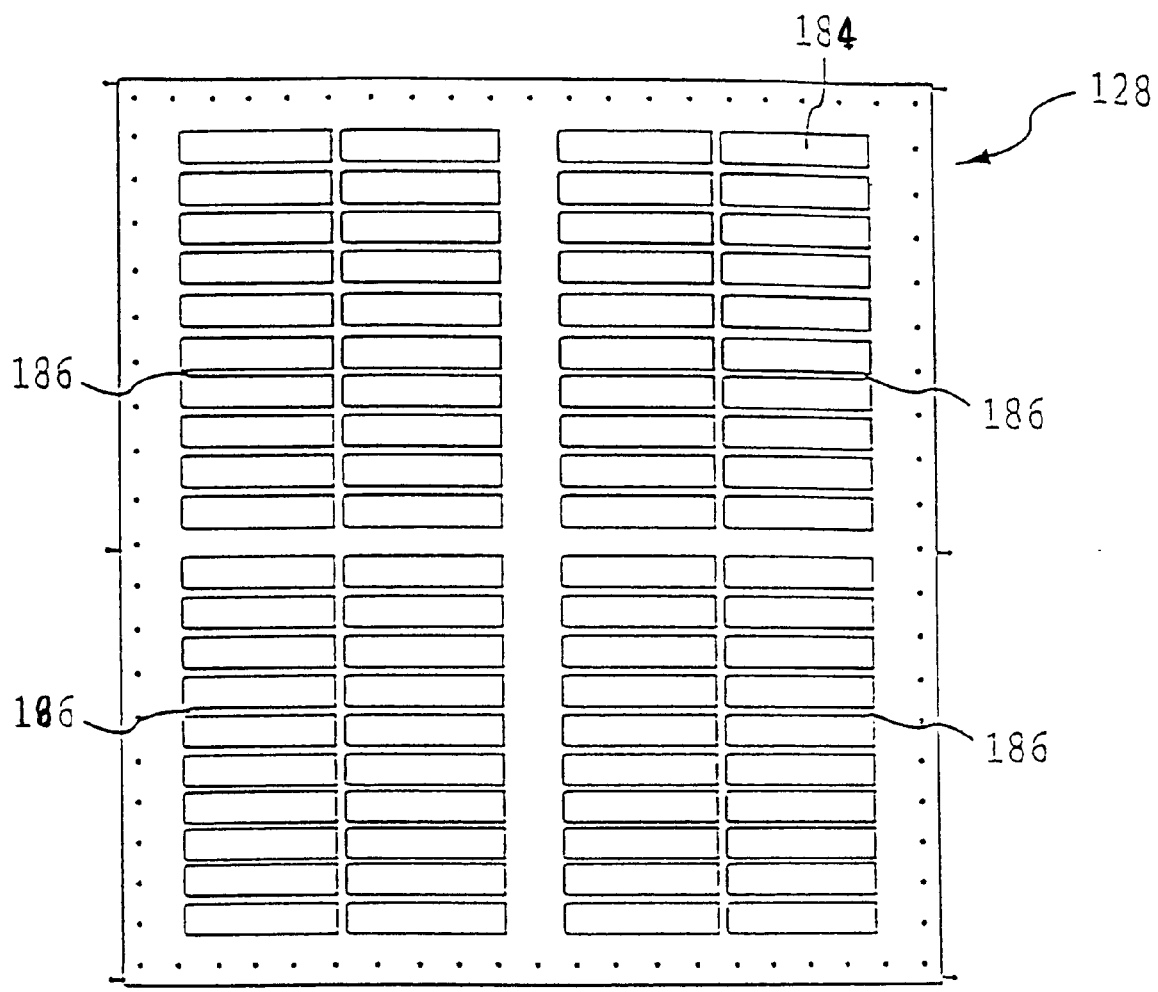
FIG. 8 is a top view of a bottom retaining plate for retaining a separator for use in an aerosol generator of the present invention.

Referring now to FIG. 8, the bottom retaining plate 128 for a 400 transducer array is shown having a design for mating with the transducer mounting plate 124 (shown in FIGS. 4–5). The bottom retaining plate 128 has eighty openings 184, arranged in four subgroups 186 of twenty openings 184 each. Each of the openings 184 corresponds with five of the transducer mounting receptacles 174 (shown in FIGS. 4–5) when the bottom retaining plate 128 is mated with the transducer mounting plate 124 to create a volume for a water bath between the transducer mounting plate 124 and the bottom retaining plate 128. The openings 184, therefore, provide a pathway for ultrasonic signals generated by ultrasonic transducers to be transmitted through the bottom retaining plate.

Figure 9:
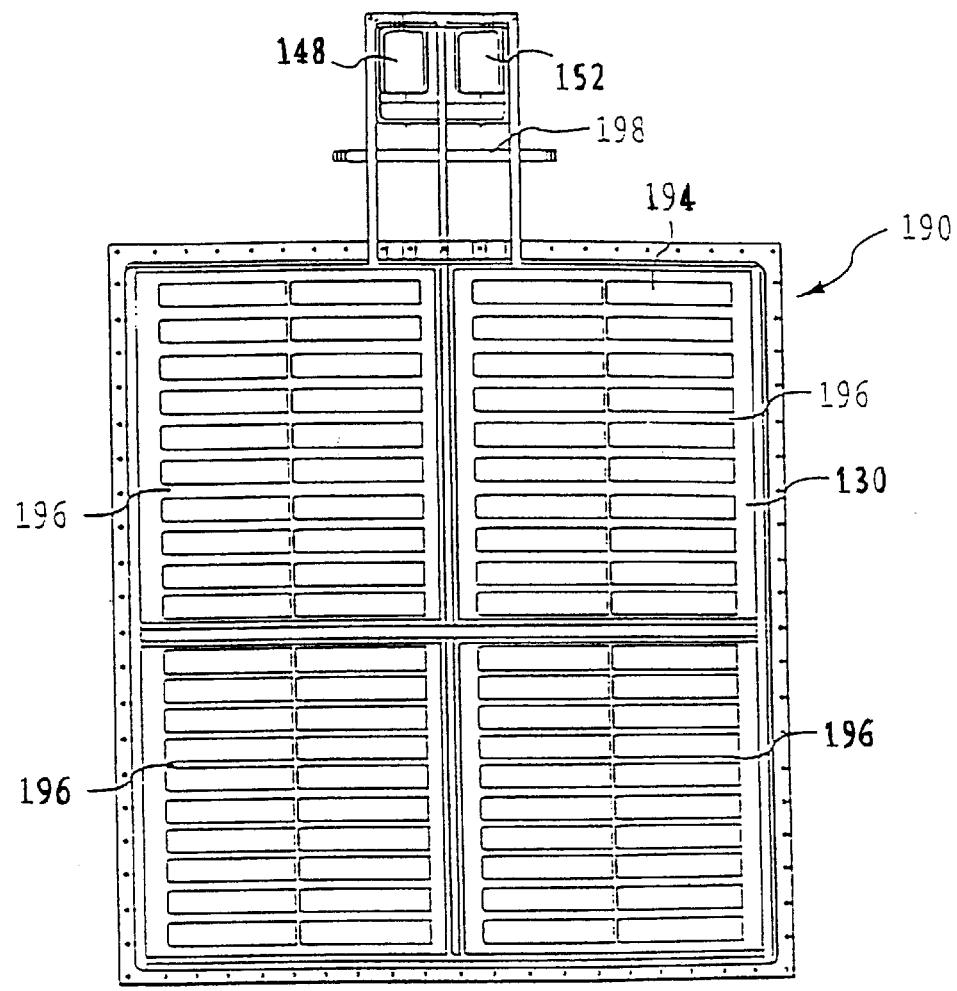
FIG. 9 is a top view of a liquid feed box having a bottom retaining plate to assist in retaining a separator for use in an aerosol generator of the present invention.
Figure 10:
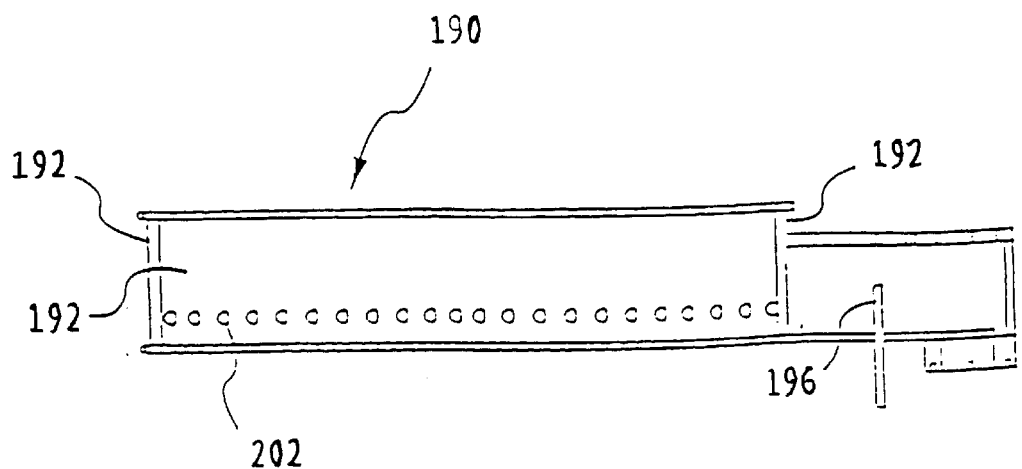
FIG. 10 is a side view of the liquid feed box shown in FIG. 9.

Referring now to FIGS. 9 and 10, a liquid feed box 190 for a 400 transducer array is shown having the top retaining plate 130 designed to fit over the bottom retaining plate 128 (shown in FIG. 8), with a separator 126 (not shown) being retained between the bottom retaining plate 128 and the top retaining plate 130 when the aerosol generator 106 is assembled. The liquid feed box 190 also includes vertically extending walls 192 for containing the liquid feed 102 when the aerosol generator is in operation. Also shown in FIGS. 9 and 10 is the feed inlet 148 and the feed outlet 152. An adjustable weir 198 determines the level of liquid feed 102 in the liquid feed box 190 during operation of the aerosol generator 106.

The top retaining plate 130 of the liquid feed box 190 has eighty openings 194 therethrough, which are arranged in four subgroups 196 of twenty openings 194 each. The openings 194 of the top retaining plate 130 correspond in size with the openings 184 of the bottom retaining plate 128 (shown in FIG. 8). When the aerosol generator 106 is assembled, the openings 194 through the top retaining plate 130 and the openings 184 through the bottom retaining plate 128 are aligned, with the separator 126 positioned therebetween, to permit transmission of ultrasonic signals when the aerosol generator 106 is in operation.

Figure 11:
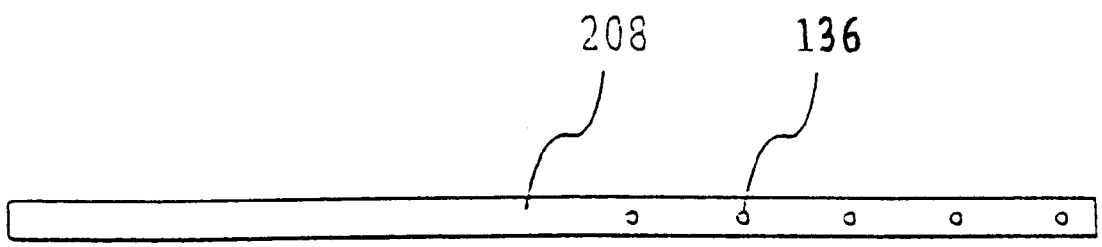
FIG. 11 is a side view of a gas tube for delivering gas within an aerosol generator of the present invention.

Referring now to FIGS. 9–11, a plurality of gas tube feed-through holes 202 extend through the vertically extending walls 192 to either side of the assembly including the feed inlet 148 and feed outlet 152 of the liquid feed box 190. The gas tube feed-through holes 202 are designed to permit insertion therethrough of gas tubes 208 of a design as shown in FIG. 11. When the aerosol generator 106 is assembled, a gas tube 208 is inserted through each of the gas tube feed-through holes 202 so that gas delivery ports 136 in the gas tube 208 will be properly positioned and aligned adjacent the openings 194 in the top retaining plate 130 for delivery of gas to atomization cones that develop in the liquid feed box 190 during operation of the aerosol generator 106. The gas delivery ports 136 are typically holes having a diameter of from about 1.5 millimeters to about 3.5 millimeters.

Figure 12:
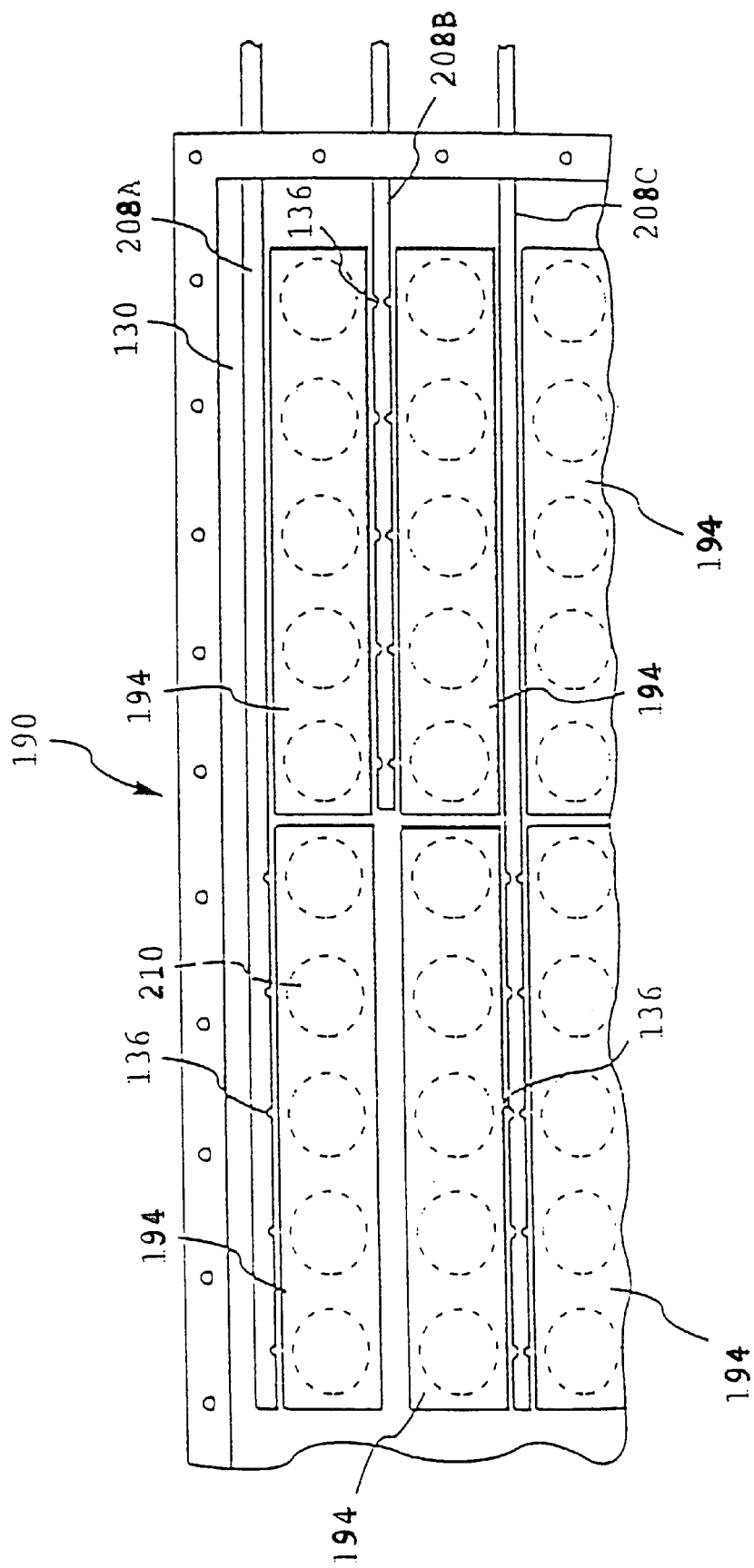
FIG. 12 shows a partial top view of gas tubes positioned in a liquid feed box for distributing gas relative to ultrasonic transducer positions for use in an aerosol generator of the present invention.

Referring now to FIG. 12, a partial view of the liquid feed box 190 is shown with gas tubes 208A, 208B and 208C positioned adjacent to the openings 194 through the top retaining plate 130. Also shown in FIG. 12 are the relative locations that ultrasonic transducer discs 120 would occupy when the aerosol generator 106 is assembled. As seen in FIG. 12, the gas tube 208A, which is at the edge of the array, has five gas delivery ports 136. Each of the gas delivery ports 136 is positioned to divert carrier gas 104 to a different one of atomization cones that develop over the array of ultrasonic transducer discs 120 when the aerosol generator 106 is operating. The gas tube 208B, which is one row in from the edge of the array, is a shorter tube that has ten gas delivery ports 136, five each on opposing sides of the gas tube 208B. The gas tube 208B, therefore, has gas delivery ports 136 for delivering gas to atomization cones corresponding with each of ten ultrasonic transducer discs 120. The third gas tube, 208C, is a longer tube that also has ten gas delivery ports 136 for delivering gas to atomization cones corresponding with ten ultrasonic transducer discs 120. The design shown in FIG. 12, therefore, includes one gas delivery port per ultrasonic transducer disc 120. Although this is a lower density of gas delivery ports 136 than for the embodiment of the aerosol generator 106 shown in FIG. 2, which includes two gas delivery ports per ultrasonic transducer disc 120, the design shown in FIG. 12 is, nevertheless, capable of producing a dense, high-quality aerosol without unnecessary waste of gas.

Figure 13:
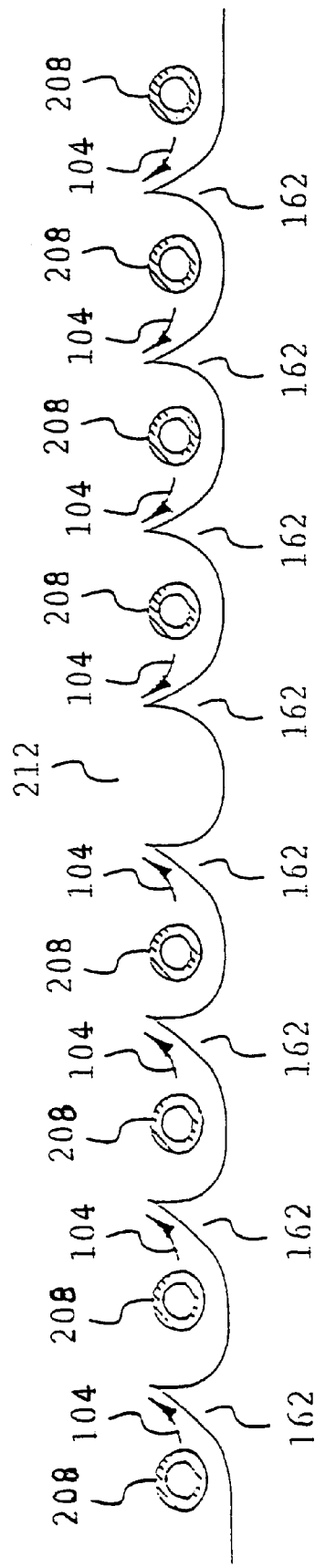
FIG. 13 shows one embodiment for a gas distribution configuration for the aerosol generator of the present invention.

Referring now to FIG. 13, the flow of carrier gas 104 relative to atomization cones 162 during operation of the aerosol generator 106 having a gas distribution configuration to deliver carrier gas 104 from gas delivery ports on both sides of the gas tubes 208, as was shown for the gas tubes 208A, 208B and 208C in the gas distribution configuration shown in FIG. 11. The carrier gas 104 sweeps both directions from each of the gas tubes 208.

Figure 14:
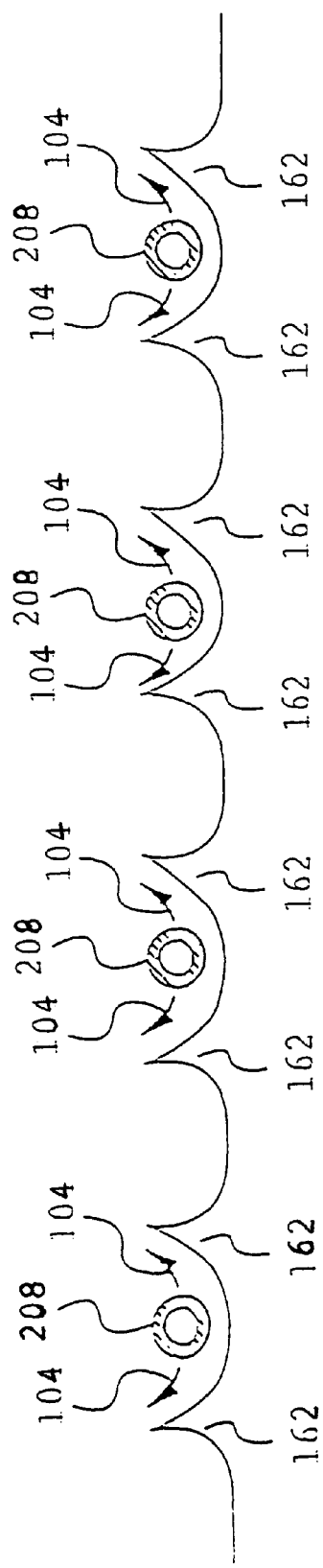
FIG. 14 shows another embodiment for a gas distribution configuration for the aerosol generator of the present invention.

An alternative, and preferred, flow for carrier gas 104 is shown in FIG. 14. As shown in FIG. 14, carrier gas 104 is delivered from only one side of each of the gas tubes 208. This results in a sweep of carrier gas from all of the gas tubes 208 toward a central area 212. This results in a more uniform flow pattern for aerosol generation that may significantly enhance the efficiency with which the carrier gas 104 is used to produce an aerosol. The aerosol that is generated, therefore, tends to be more heavily loaded with liquid droplets.

Figure 15:
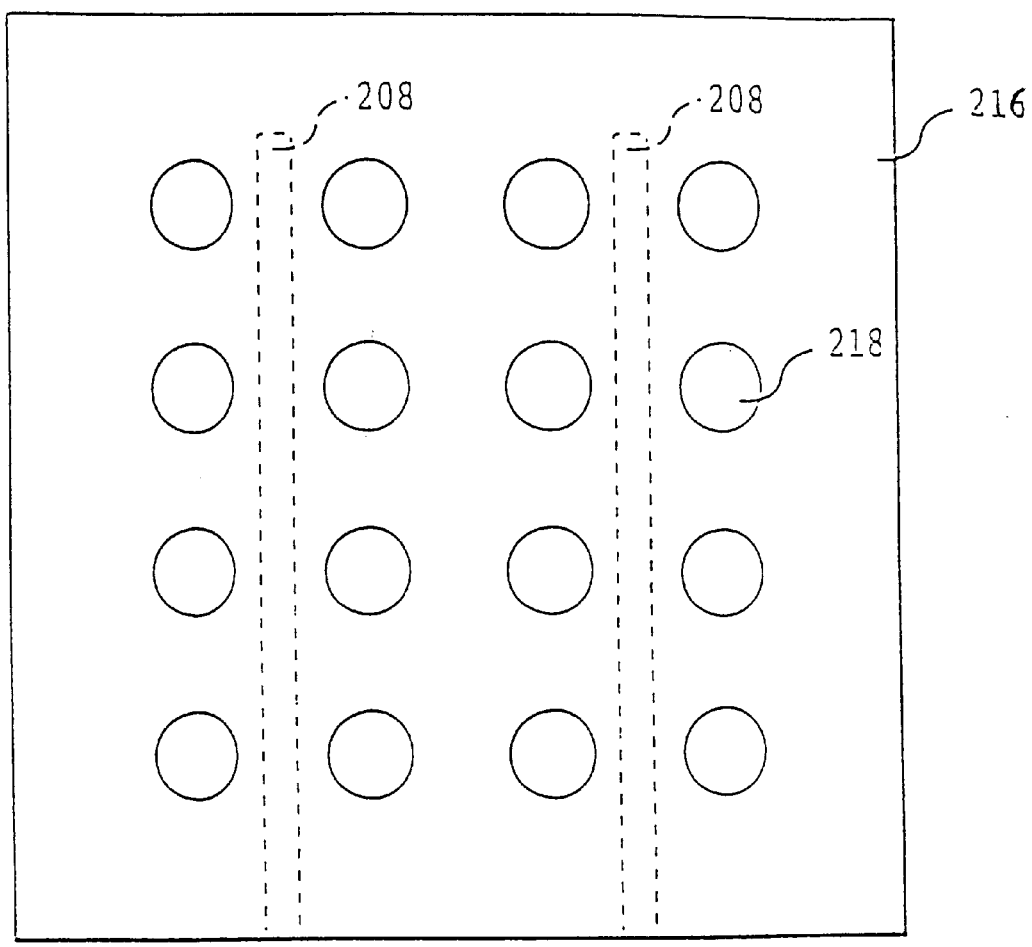
Figure 16:
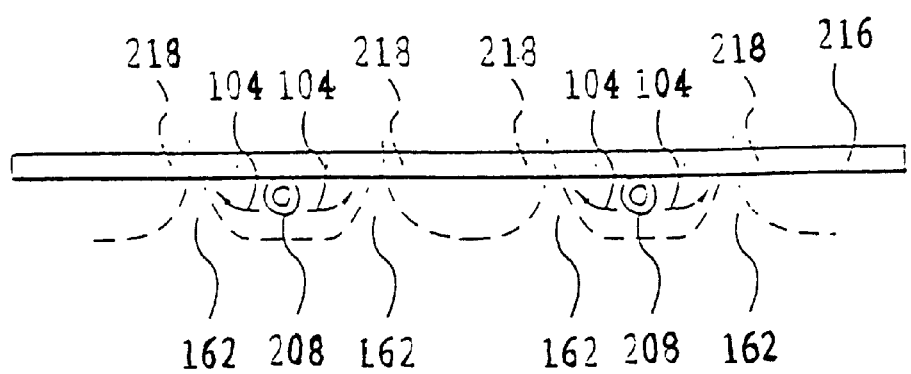

Another configuration for distributing carrier gas in the aerosol generator 106 is shown in FIGS. 15 and 16. In this configuration, the gas tubes 208 are hung from a gas distribution plate 216 adjacent gas flow holes 218 through the gas distribution plate 216. In the aerosol generator 106, the gas distribution plate 216 would be mounted above the liquid feed, with the gas flow holes positioned to each correspond with an underlying ultrasonic transducer. Referring specifically to FIG. 16, when the ultrasonic generator 106 is in operation, atomization cones 162 develop through the gas flow holes 218, and the gas tubes 208 are located such that carrier gas 104 exiting from ports in the gas tubes 208 impinge on the atomization cones and flow upward through the gas flow holes. The gas low holes 218, therefore, act to assist in efficiently distributing the carrier gas 104 about the atomization cones 162 for aerosol formation. It should be appreciated that the gas distribution plates 218 can be made to accommodate any number of the gas tubes 208 and gas flow holes 218. For convenience of illustration, the embodiment shown in FIGS. 15 and 16 shows a design having only two of the gas tubes 208 and only 16 of the gas flow holes 218. Also, it should be appreciated that the gas distribution plate 216 could be used alone, without the gas tubes 208. In that case, a slight positive pressure of carrier gas 104 would be maintained under the gas distribution plate 216 and the gas flow holes 218 would be sized to maintain the proper velocity of carrier gas 104 through the gas flow holes 218 for efficient aerosol generation. Because of the relative complexity of operating in that mode, however, it is not preferred.

Figure 17:
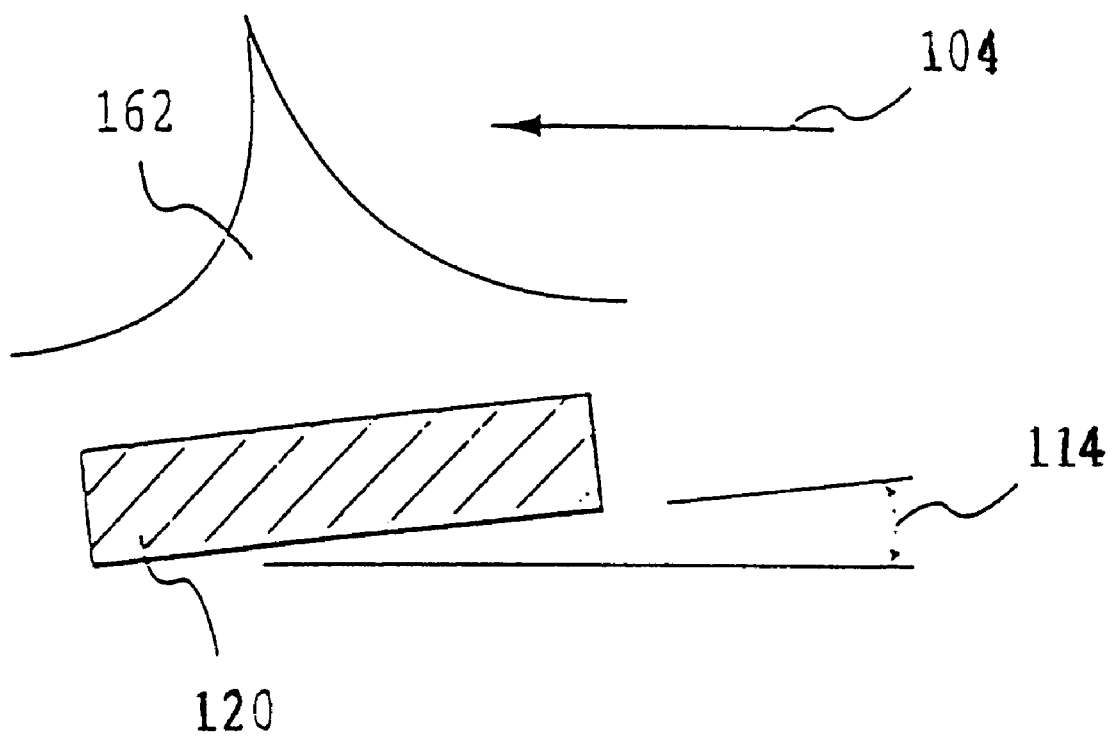

Aerosol generation may also be enhanced through mounting of ultrasonic transducers at a slight angle and directing the carrier gas at resulting atomization cones such that the atomization cones are tilting in the same direction as the direction of flow of carrier gas. Referring to FIG. 17, an ultrasonic transducer disc 120 is shown. The ultrasonic transducer disc 120 is tilted at a tilt angle 114 (typically less than 10 degrees), so that the atomization cone 162 will also have a tilt. It is preferred that the direction of flow of the carrier gas 104 directed at the atomization cone 162 is in the same direction as the tilt of the atomization cone 162.

Figure 18:
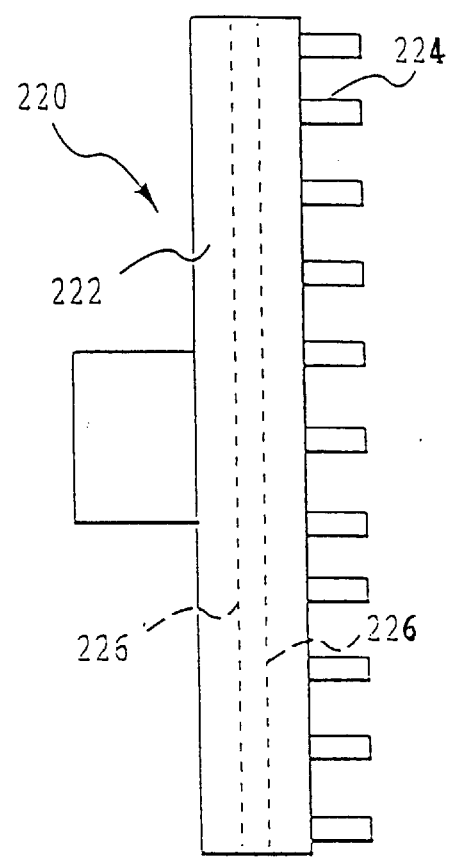
Figure 19:
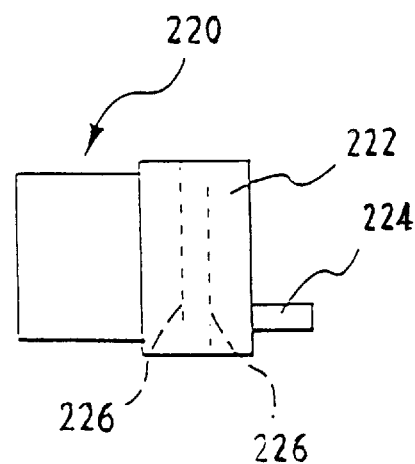

Referring now to FIGS. 18 and 19, a gas manifold 220 is shown for distributing gas to the gas tubes 208 in a 400 transducer array design. The gas manifold 220 includes a gas distribution box 222 and piping stubs 224 for connection with gas tubes 208 (shown in FIG. 11). Inside the gas distribution box 222 are two gas distribution plates 226 that form a flow path to assist in distributing the gas equally throughout the gas distribution box 222, to promote substantially equal delivery of gas through the piping stubs 224. The gas manifold 220, as shown in FIGS. 18 and 19, is designed to feed eleven gas tubes 208. For the 400 transducer design, a total of four gas manifolds 220 are required.

Figure 20:
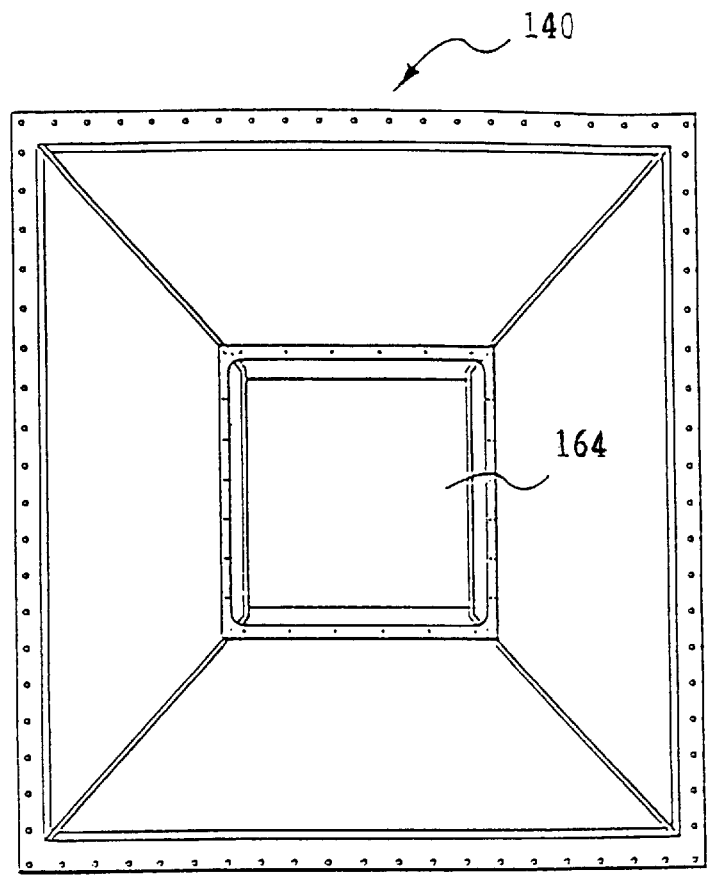
Figure 21:
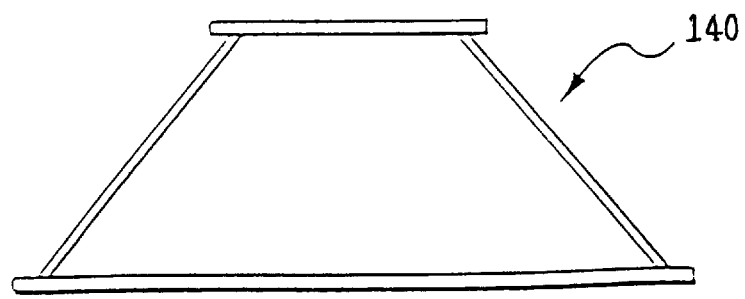

Referring now to FIGS. 20 and 21, the generator lid 140 is shown for a 400 transducer array design. The generator lid 140 mates with and covers the liquid feed box 190 (shown in FIGS. 9 and 10). The generator lid 140, as shown in FIGS. 20 and 21, has a hood design to permit easy collection of the aerosol 108 without subjecting droplets in the aerosol 108 to sharp edges on which droplets may coalesce and be lost, and possibly interfere with the proper operation of the aerosol generator 106. When the aerosol generator 106 is in operation, the aerosol 108 would be withdrawn via the aerosol exit opening 164 through the generator cover 140.

It is important that the aerosol stream that is fed to the furnace 110 have a high droplet flow rate and high droplet loading as would be required for most industrial applications. With the present invention, the aerosol stream fed to the furnace preferably includes a droplet flow of greater than about 0.5 liters per hour, more preferably greater than about 2 liters per hour, still more preferably greater than about 5 liters per hour, even more preferably greater than about 10 liters per hour, particularly greater than about 50 liters per hour and most preferably greater than about 100 liters per hour; and with the droplet loading being typically greater than about 0.04 milliliters of droplets per liter of carrier gas, preferably greater than about 0.083 milliliters of droplets per liter of carrier gas 104, more preferably greater than about 0.167 milliliters of droplets per liter of carrier gas 104, still more preferably greater than about 0.25 milliliters of droplets per liter of carrier gas 104, particularly greater than about 0.33 milliliters of droplets per liter of carrier gas 104 and most preferably greater than about 0.83 milliliters of droplets per liter of carrier gas 104.

As discussed previously, the aerosol generator 106 of the present invention produces a concentrated, high quality aerosol of micro-sized droplets having a relatively narrow size distribution. However, the process of the present invention can be enhanced by further classifying by size the droplets in the aerosol 108 prior to introduction of the droplets into the furnace 110. In this manner, the size and size distribution of particles in the particulate product 116 are further controlled.

Figure 22:
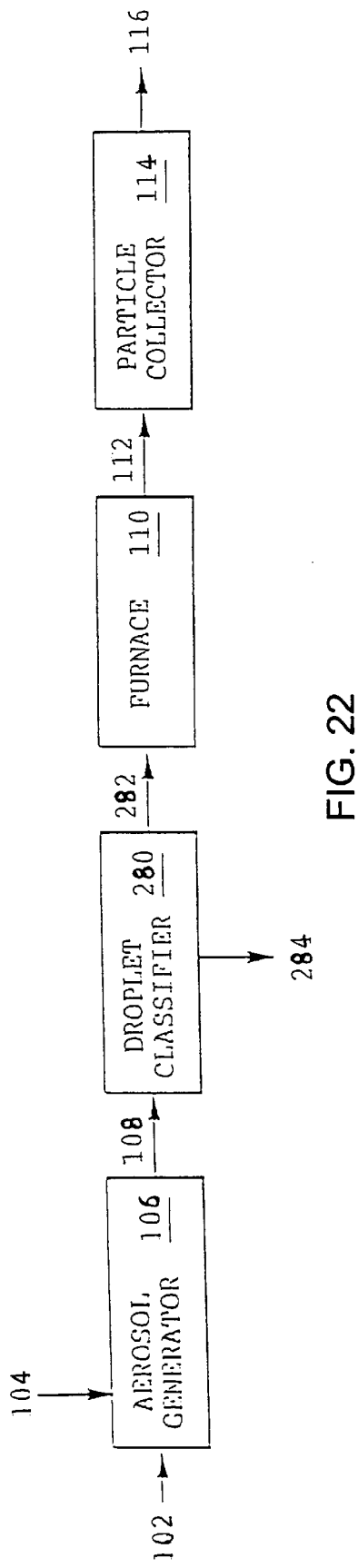

Referring now to FIG. 22, a process flow diagram is shown for one embodiment of the process of the present invention including such droplet classification. As shown in FIG. 22, the aerosol 108 from the aerosol generator 106 goes to a droplet classifier 280 where oversized droplets are removed from the aerosol 108 to prepare a classified aerosol 282. Liquid 284 from the oversized droplets that are being removed is drained from the droplet classifier 280. This drained liquid 284 may advantageously be recycled for use in preparing additional liquid feed 102.

Any suitable droplet classifier may be used for removing droplets above a predetermined size. For example, a cyclone could be used to remove over-size droplets. A preferred droplet classifier for many applications, however, is an impactor. One embodiment of an impactor for use with the present invention will now be described with reference to FIGS. 23–27.

Figure 23:
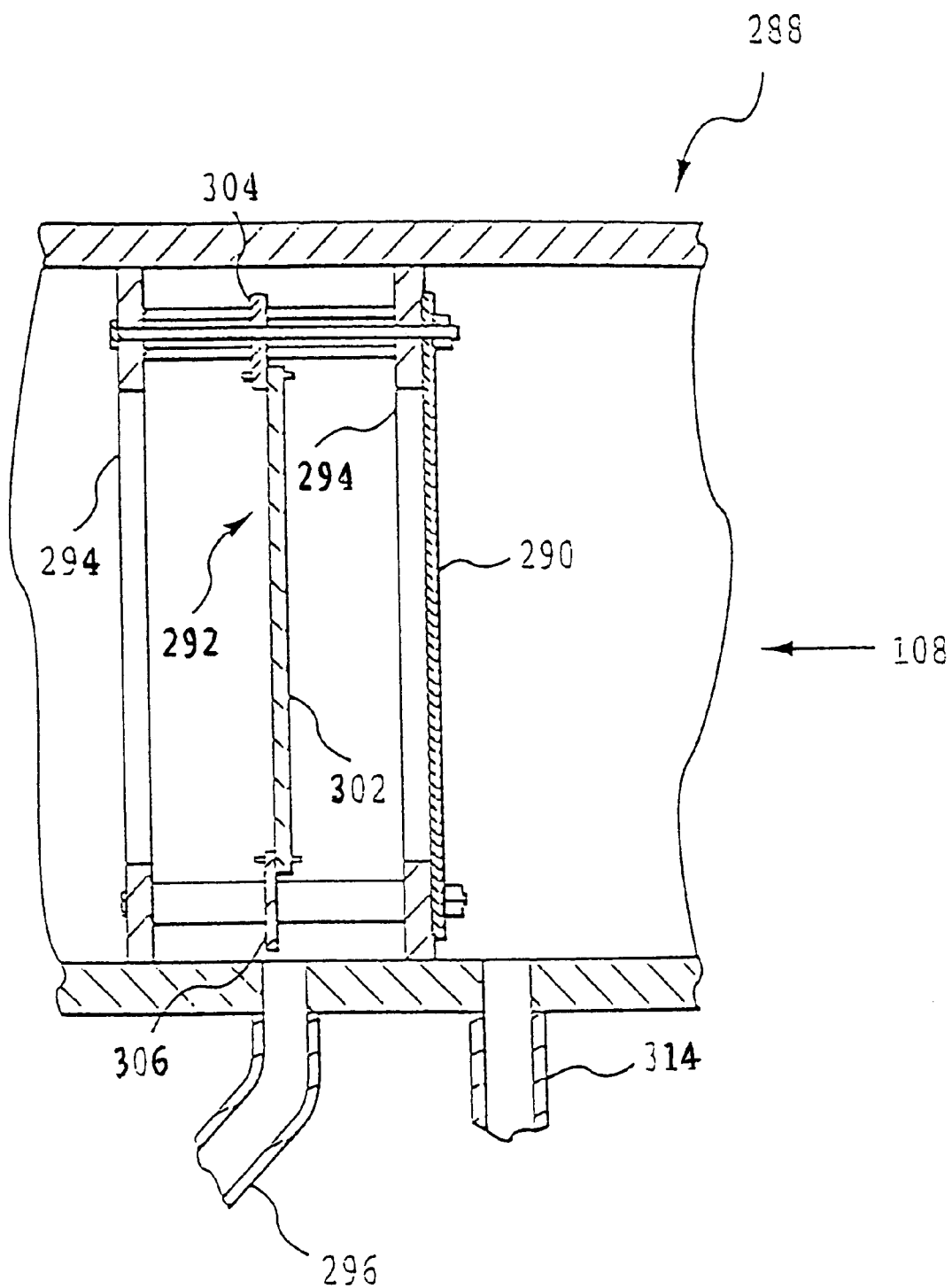

As seen in FIG. 23, an impactor 288 has disposed in a flow conduit 286 a flow control plate 290 and an impactor plate assembly 292. The flow control plate 290 is conveniently mounted on a mounting plate 294.

Figure 24:
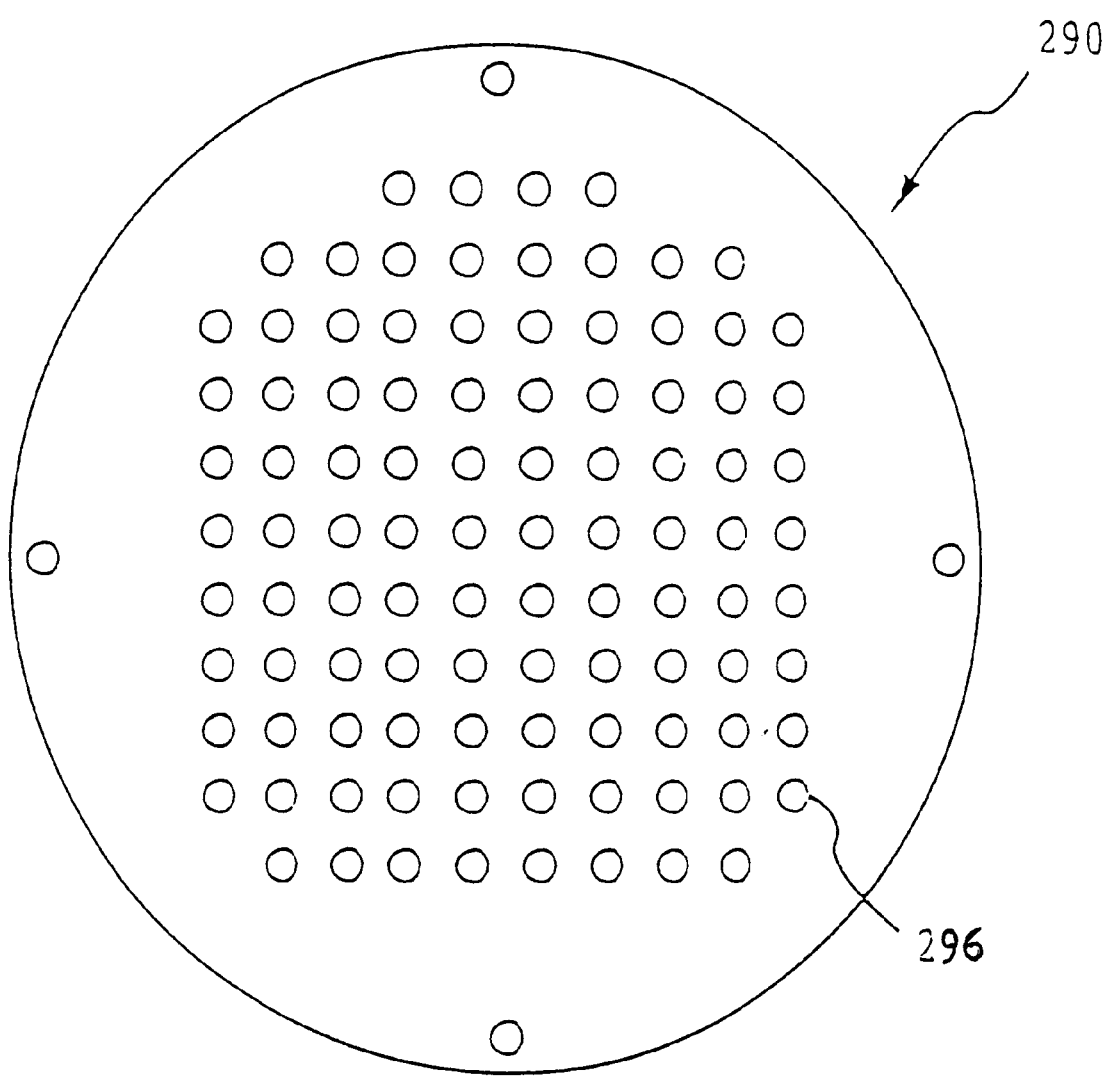

The flow control plate 290 is used to channel the flow of the aerosol stream toward the impactor plate assembly 292 in a manner with controlled flow characteristics that are desirable for proper impaction of oversize droplets on the impactor plate assembly 292 for removal through the drains 296 and 314. One embodiment of the flow control plate 290 is shown in FIG. 24. The flow control plate 290 has an array of circular flow ports 296 for channeling flow of the aerosol 108 towards the impactor plate assembly 292 with the desired flow characteristics.

Figure 25:
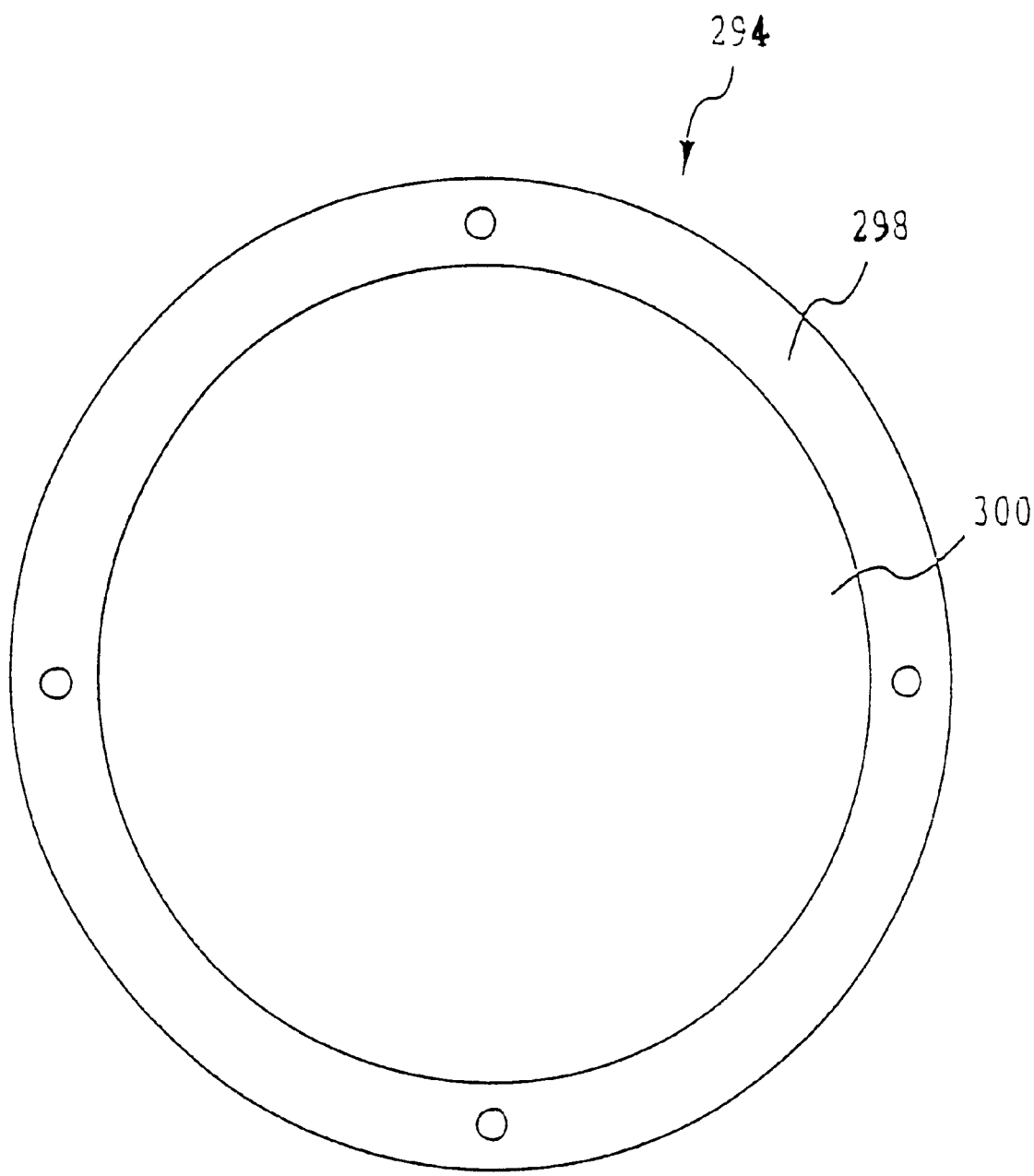

Details of the mounting plate 294 are shown in FIG. 25. The mounting plate 294 has a mounting flange 298 with a large diameter flow opening 300 passing therethrough to permit access of the aerosol 108 to the flow ports 296 of the flow control plate 290 (shown in FIG. 24).

Figure 26:
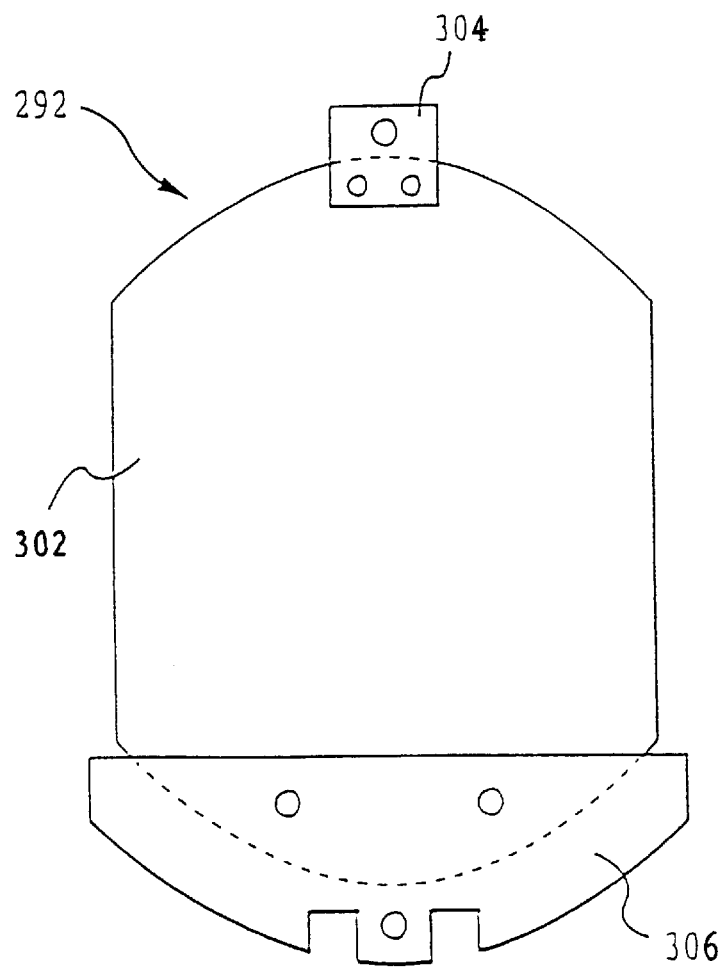
Figure 27:
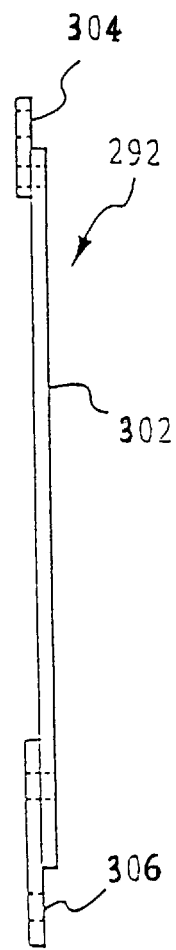
Figure 28:
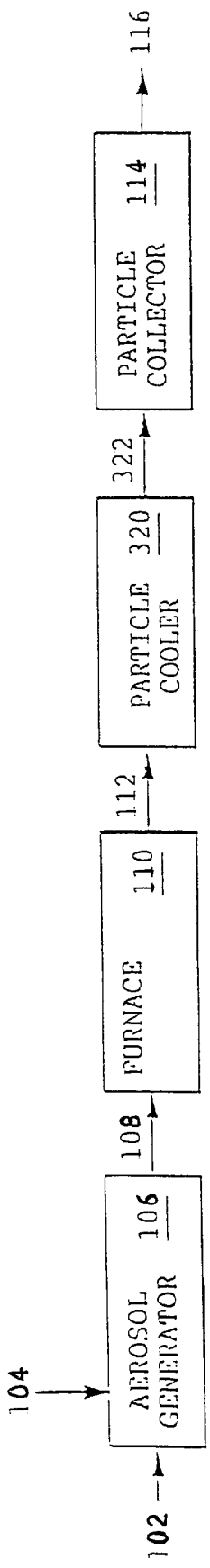

Referring now to FIGS. 26 and 27, one embodiment of an impactor plate assembly 292 is shown. The impactor plate assembly 292 includes an impactor plate 302 and mounting brackets 304 and 306 used to mount the impactor plate 302 inside of the flow conduit 286. The impactor plate 302 and the flow channel plate 290 are designed so that droplets larger than a predetermined size will have momentum that is too large for those particles to change flow direction to navigate around the impactor plate 302.

During operation of the impactor 288, the aerosol 108 from the aerosol generator 106 passes through the upstream flow control plate 290. Most of the droplets in the aerosol navigate around the impactor plate 302 and exit the impactor 288 through the downstream flow control plate 290 in the classified aerosol 282. Droplets in the aerosol 108 that are too large to navigate around the impactor plate 302 will impact on the impactor plate 302 and drain through the drain 296 to be collected with the drained liquid 284 (as shown in FIG. 23).

The configuration of the impactor plate 302 shown in FIG. 22 represents only one of many possible configurations for the impactor plate 302. For example, the impactor 288 could include an upstream flow control plate 290 having vertically extending flow slits therethrough that are offset from vertically extending flow slits through the impactor plate 302, such that droplets too large to navigate the change in flow due to the offset of the flow slits between the flow control plate 290 and the impactor plate 302 would impact on the impactor plate 302 to be drained away. Other designs are also possible.

Figure 32:
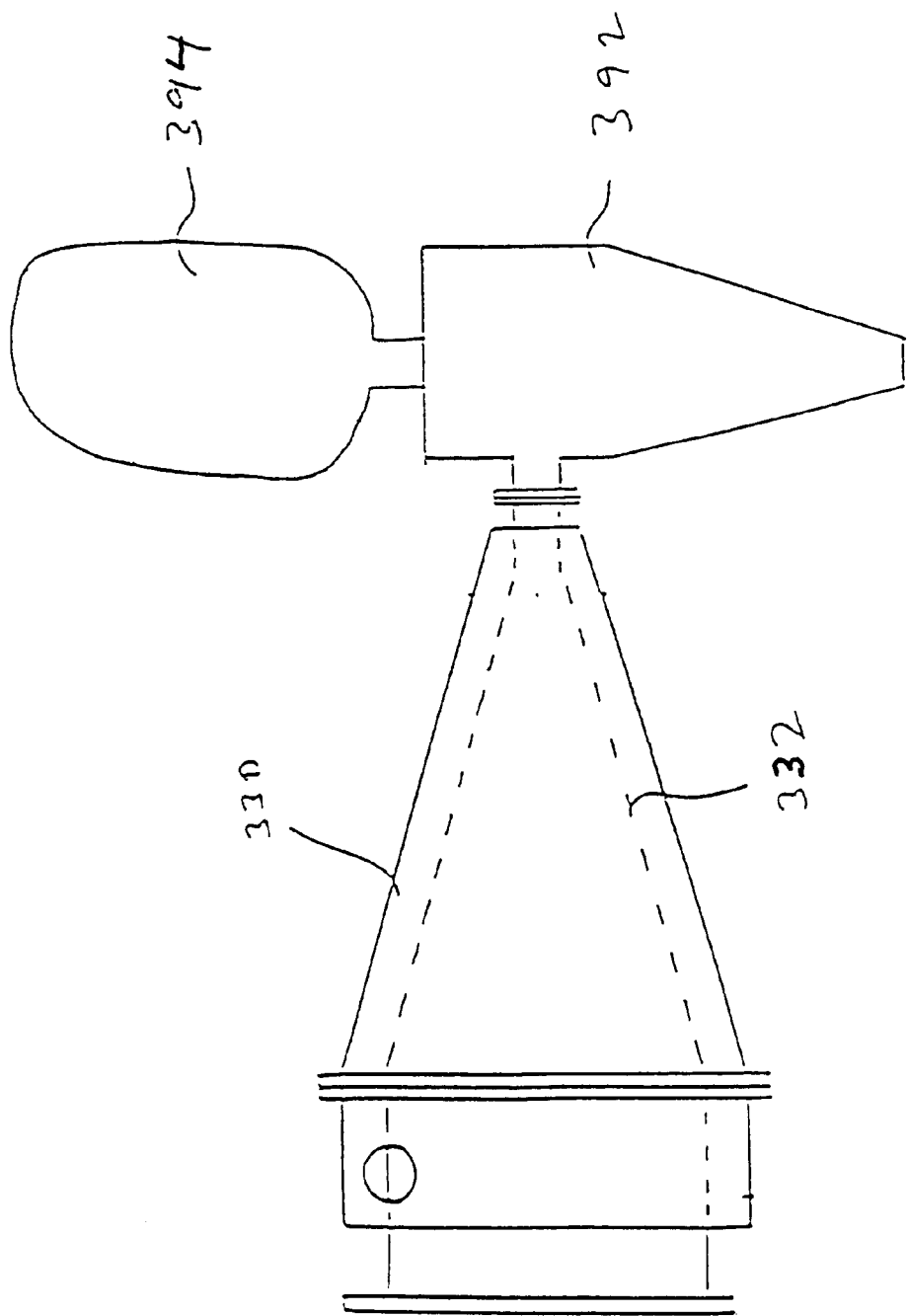

In a preferred embodiment of the present invention, the droplet classifier 280 is typically designed to remove droplets from the aerosol 108 that are larger than about 15 $\mu$m, more preferably to remove droplets larger than about 10 $\mu$m, even more preferably to remove droplets of a size larger than about 8 $\mu$m and most preferably to remove droplets larger than about 5 $\mu$m. The droplet classification size in the droplet classifier is preferably smaller than about 15 $\mu$m, more preferably smaller than about 10 $\mu$m, even more preferably smaller than about 8 $\mu$m and most preferably smaller than about 5 $\mu$m. The classification size, also called the classification cut point, is that size at which half of the droplets of that size are removed and half of the droplets of that size are retained. Depending upon the specific application, however, the droplet classification size may be varied, such as by changing the spacing between the impactor plate 302 and the flow control plate 290 or increasing or decreasing aerosol velocity through the jets in the flow control plate 290. Because the aerosol generator 106 of the present invention initially produces a high quality aerosol 108, having a relatively narrow size distribution of droplets, typically less than about 30 weight percent of liquid feed 102 in the aerosol 108 is removed as the drain liquid 284 in the droplet classifier 288, with preferably less than about 25 weight percent being removed, even more preferably less than about 20 weight percent being removed and most preferably less than about 15 weight percent being removed. Minimizing the removal of liquid feed 102 from the aerosol 108 is particularly important for commercial applications to increase the yield of high quality particulate product 116. It should be noted, however, that because of the superior performance of the aerosol generator 106, it is typically not required to use an impactor or other droplet classifier to obtain a suitable aerosol. This is a major advantage, because the added complexity and liquid losses accompanying use of an impactor may often be avoided with the process of the present invention.

With some applications of the process of the present invention, it may be possible to collect the glass particles 112 directly from the output of the furnace 110. More often, however, it will be desirable to cool the glass particles 112 exiting the furnace 110 prior to collection of the particles 112 in the particle collector 114. Referring now to FIG. 28, one embodiment of the process of the present invention is shown in which the particles 112 exiting the furnace 110 are sent to a particle cooler 320 to produce a cooled particle stream 322, which is then fed to the particle collector 114. Although the particle cooler 320 may be any cooling apparatus capable of cooling the particles 112 to the desired temperature for introduction into the particle collector 114, traditional heat exchanger designs are not preferred. This is because a traditional heat exchanger design ordinarily directly subjects the aerosol stream, in which the hot particles 112 are suspended, to cool surfaces. In that situation, significant losses of the particles 112 occur due to thermophoretic deposition of the hot particles 112 on the cool surfaces of the heat exchanger. According to the present invention, a gas quench apparatus is provided for use as the particle cooler 320 that significantly reduces thermophoretic losses compared to a traditional heat exchanger.

Referring now to FIGS. 29–31, one embodiment of a gas quench cooler 330 is shown. The gas quench cooler includes a perforated conduit 332 housed inside of a cooler housing 334 with an annular space 336 located between the cooler housing 334 and the perforated conduit 332. In fluid communication with the annular space 336 is a quench gas inlet box 338, inside of which is disposed a portion of an aerosol outlet conduit 340. The perforated conduit 332 extends between the aerosol outlet conduit 340 and an aerosol inlet conduit 342. Attached to an opening into the quench gas inlet box 338 are two quench gas feed tubes 344. Referring specifically to FIG. 31, the perforated tube 332 is shown. The perforated tube 332 has a plurality of openings 345. The openings 345, when the perforated conduit 332 is assembled into the gas quench cooler 330, permit the flow of quench gas 346 from the annular space 336 into the interior space 348 of the perforated conduit 332. Although the openings 345 are shown as being round holes, any shape of opening could be used, such as slits. Also, the perforated conduit 332 could be a porous screen. Two heat radiation shields 347 prevent downstream radiant heating from the furnace. In most instances, however, it will not be necessary to include the heat radiation shields 347, because downstream radiant heating from the furnace is normally not a significant problem. Use of the heat radiation shields 347 is not preferred due to particulate losses that accompany their use.

With continued reference to FIGS. 29–31, operation of the gas quench cooler 330 will now be described. During operation, the particles 112, carried by and dispersed in a gas stream, enter the gas quench cooler 330 through the aerosol inlet conduit 342 and flow into the interior space 348 of perforated conduit 332. Quench gas 346 is introduced through the quench gas feed tubes 344 into the quench gas inlet box 338. Quench gas 346 entering the quench gas inlet box 338 encounters the outer surface of the aerosol outlet conduit 340, forcing the quench gas 346 to flow, in a spiraling, swirling manner, into the annular space 336, where the quench gas 346 flows through the openings 345 through the walls of the perforated conduit 332. Preferably, the gas 346 retains some swirling motion even after passing into the interior space 348. In this way, the particles 112 are quickly cooled with low losses of particles to the walls of the gas quench cooler 330. In this manner, the quench gas 346 enters in a radial direction into the interior space 348 of the perforated conduit 332 around the entire periphery, or circumference, of the perforated conduit 332 and over the entire length of the perforated conduit 332. The cool quench gas 346 mixes with and cools the hot particles 112, which then exit through the aerosol outlet conduit 340 as the cooled particle stream 322. The cooled particle stream 322 can then be sent to the particle collector 114 for particle collection. The temperature of the cooled particle stream 322 is controlled by introducing more or less quench gas. Also, as shown in FIG. 29, the quench gas 346 is fed into the quench cooler 330 in counter flow to flow of the particles. Alternatively, the quench cooler could be designed so that the quench gas 346 is fed into the quench cooler in concurrent flow with the flow of the particles 112. The amount of quench gas 346 fed to the gas quench cooler 330 will depend upon the specific material being made and the specific operating conditions. The quantity of quench gas 346 used, however, must be sufficient to reduce the temperature of the aerosol steam including the particles 112 to the desired temperature. Typically, the particles 112 are cooled to a temperature at least below about 200° C., and often lower. The only limitation on how much the particles 112 are cooled is that the cooled particle stream 322 must be at a temperature that is above the condensation temperature for water as another condensible vapor in the stream. The temperature of the cooled particle stream 322 is often at a temperature of from about 50° C. to about 120° C.

Because of the entry of quench gas 346 into the interior space 348 of the perforated conduit 322 in a radial direction about the entire circumference and length of the perforated conduit 322, a buffer of the cool quench gas 346 is formed about the inner wall of the perforated conduit 332, thereby significantly inhibiting the loss of hot particles 112 due to thermophoretic deposition on the cool wall of the perforated conduit 332. In operation, the quench gas 346 exiting the openings 345 and entering into the interior space 348 should have a radial velocity (velocity inward toward the center of the circular cross-section of the perforated conduit 332) of larger than the thermophoretic velocity of the particles 112 inside the perforated conduit 332 in a direction radially outward toward the perforated wall of the perforated conduit 332.

As seen in FIGS. 29–31, the gas quench cooler 330 includes a flow path for the particles 112 through the gas quench cooler of a substantially constant cross-sectional shape and area. Preferably, the flow path through the gas quench cooler 330 will have the same cross-sectional shape and area as the flow path through the furnace 110 and through the conduit delivering the aerosol 108 from the aerosol generator 106 to the furnace 110. In one embodiment, however, it may be necessary to reduce the cross-sectional area available for flow prior to the particle collector 114. This is the case, for example, when the particle collector includes a cyclone for separating particles in the cooled particle stream 322 from gas in the cooled particle stream 322. This is because of the high inlet velocity requirements into cyclone separators.

Referring now to FIG. 32, one embodiment of the gas quench cooler 330 is shown in combination with a cyclone separator 392. The perforated conduit 332 has a continuously decreasing cross-sectional area for flow to increase the velocity of flow to the proper value for the feed to cyclone separator 392. Attached to the cyclone separator 392 is a bag filter 394 for final clean-up of overflow from the cyclone separator 392. Separated particles exit with underflow from the cyclone separator 392 and may be collected in any convenient container. The use of cyclone separation is particularly preferred for glass powder batches having a weight average size of larger than about 1 μm, although a series of cyclones may be needed to obtain the desired degree of separation. Cyclone separation is particularly preferred for powders having a weight average size of larger than about 1.5 μm.

Figure 33:
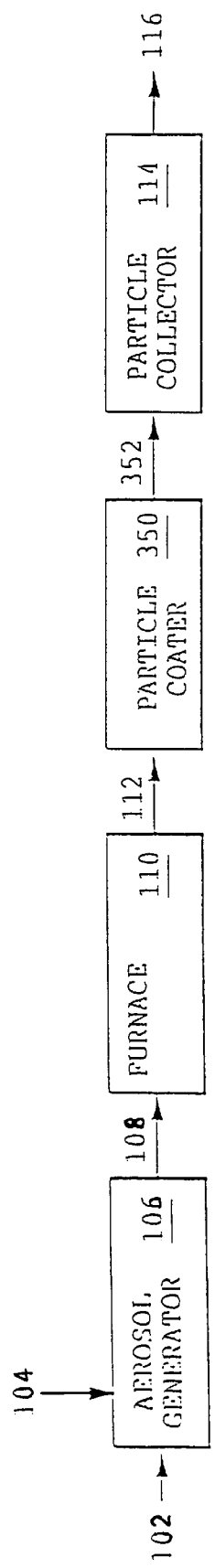

In an additional embodiment, the process of the present invention can also incorporate compositional modification of the glass particles 112 exiting the furnace. Most commonly, the compositional modification will involve forming on the glass particles 112 a material phase that is different than that of the particles 112, such as by coating the glass particles 112 with a coating material. One embodiment of the process of the present invention incorporating particle coating is shown in FIG. 33. As shown in FIG. 33, the glass particles 112 exiting from the furnace 110 go to a particle coater 350 where a coating is placed over the outer surface of the glass particles 112 to form coated particles 352, which are then sent to the particle collector 114 for preparation of the particulate product 116. Coating methodologies employed in the particle coater 350 are discussed in more detail below.

With continued reference primarily to FIG. 33, in a preferred embodiment, when the particles 112 are coated according to the process of the present invention, the particles 112 are also manufactured via the aerosol process of the present invention, as previously described. The process of the present invention can, however, be used to coat particles that have been premanufactured by a different process. When coating particles that have been premanufactured by a different route, such as by liquid precipitation, it is preferred that the particles remain in a dispersed state from the time of manufacture to the time that the particles are introduced in slurry form into the aerosol generator 106 for preparation of the aerosol 108 to form the dry particles 112 in the furnace 110, which particles 112 can then be coated in the particle coater 350. Maintaining particles in a dispersed state from manufacture through coating avoids problems associated with agglomeration and redispersion of particles if particles must be redispersed in the liquid feed 102 for feed to the aerosol generator 106. For example, for particles originally precipitated from a liquid medium, the liquid medium containing the suspended precipitated glass particles could be used to form the liquid feed 102 to the aerosol generator 106. It should be noted that the particle coater 350 could be an integral extension of the furnace 110 or could be a separate piece of equipment.

Figure 34:
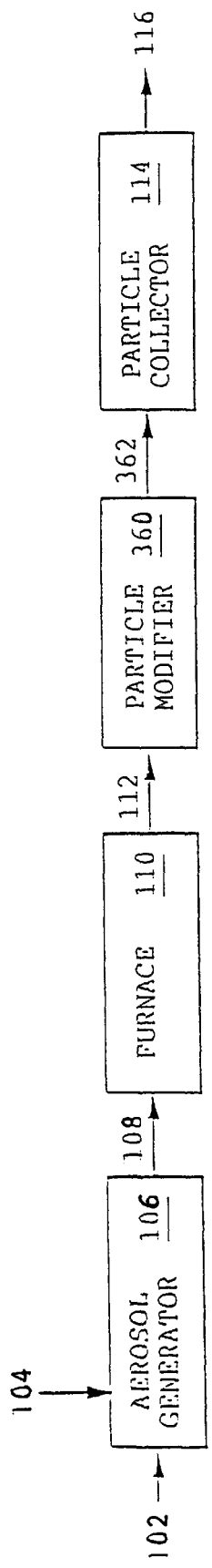
Figure 35A:
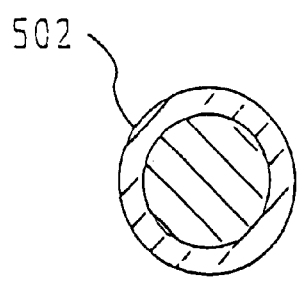
Figure 35B:
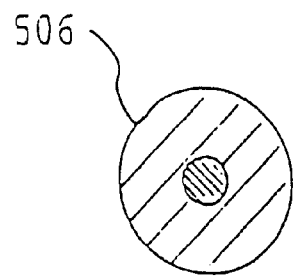
Figure 35C:
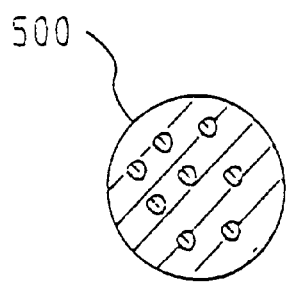
Figure 35D:
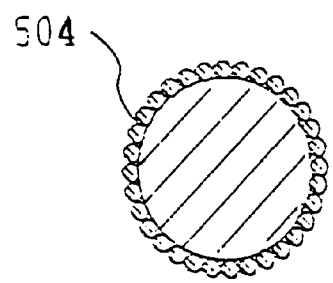
Figure 35E:
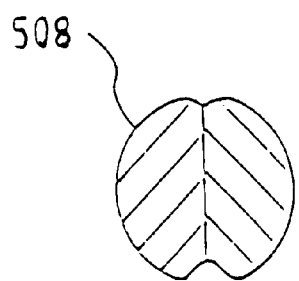
Figure 35F:
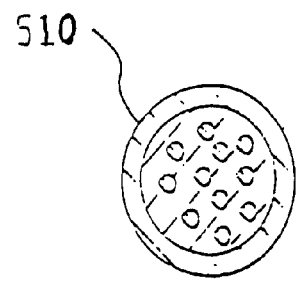

In a further embodiment of the present invention, following preparation of the particles 112 in the furnace 110, the particles 112 may then be structurally modified to impart desired physical properties prior to particle collection. Referring now to FIG. 34, one embodiment of the process of the present invention is shown including such structural particle modification. The particles 112 exiting the furnace 110 go to a particle modifier 360 where the particles are structurally modified to form modified particles 362, which are then sent to the particle collector 114 for preparation of the particulate product 116. The particle modifier 360 is typically a furnace, such as an annealing furnace, which may be integral with the furnace 110 or may be a separate heating device. Regardless, it is important that the particle modifier 360 have temperature control that is independent of the furnace 110, so that the proper conditions for particle modification may be provided separate from conditions required of the furnace 110 to prepare the glass particles 112. The particle modifier 360, therefore, typically provides a temperature controlled environment and necessary residence time to effect the desired structural modification of the particles 112.

The structural modification that occurs in the particle modifier 360 may be any modification to the structure or morphology of the particles 112. For example, the particles 112 may be annealed in the particle modifier 360 to densify the glass particles 112 or to recrystallize the glass particles 112 into a polycrystalline form.

The initial morphology of composite particles made in the furnace 110, according to the present invention, could take a variety of forms, depending upon the specified materials involved and the specific processing conditions. Examples of some possible composite particle morphologies, manufacturable according to the present invention are shown in FIG. 35. These morphologies could be of the particles as initially produced in the furnace 110 or that result from structural modification in the particle modifier 360. Furthermore, the composite particles could include a mixture of the morphological attributes shown in FIG. 35.

Aerosol generation with the process of the present invention has thus far been described with respect to the ultrasonic aerosol generator. Use of the ultrasonic generator is preferred for the process of the present invention because of the extremely high quality and dense aerosol generated. In some instances, however, the aerosol generation for the process of the present invention may have a different design depending upon the specific application. For example, when larger particles are desired, such as those having a weight average size of larger than about 3 μm, a spray nozzle atomizer may be preferred. For smaller-particle applications, however, and particularly for those applications to produce particles smaller than about 3 μm, as is generally desired with the particles of the present invention, an ultrasonic generator, as described herein, is particularly preferred. In that regard, the ultrasonic generator of the present invention is particularly preferred for when making particles with a weight average size of from about 0.1 μm to about 3 μm.

Although ultrasonic aerosol generators have been used for medical applications and home humidifiers, use of ultrasonic generators for spray pyrolysis particle manufacture has largely been confined to small-scale, experimental situations. The ultrasonic aerosol generator of the present invention described with reference to FIGS. 2–21, however, is well suited for commercial production of high quality powders with a small average size and a narrow size distribution. In that regard, the aerosol generator produces a high quality aerosol, with heavy droplet loading and at a high rate of production. Such a combination of small droplet size, narrow size distribution, heavy droplet loading, and high production rate provide significant advantages over existing aerosol generators that usually suffer from at least one of inadequately narrow size distribution, undesirably low droplet loading, or unacceptably low production rate.

Through the careful and controlled design of the ultrasonic generator of the present invention, an aerosol may be produced typically having greater than about 70 weight percent (and preferably greater than about 80 weight percent) of droplets in the size range of from about 1 μm to about 10 μm, preferably in a size range of from about 1 μm to about 5 μm and more preferably from about 2 μm to about 4 μm. Also, the ultrasonic generator of the present invention is capable of delivering high output rates of liquid feed in the aerosol. The rate of liquid feed, at the high liquid loadings previously described, is preferably greater than about 25 milliliters per hour per transducer, more preferably greater than about 37.5 milliliters per hour per transducer, even more preferably greater than about 50 milliliters per hour per transducer and most preferably greater than about 100 millimeters per hour per transducer. This high level of performance is desirable for commercial operations and is accomplished with the present invention with a relatively simple design including a single precursor bath over an array of ultrasonic transducers. The ultrasonic generator is made for high aerosol production rates at a high droplet loading, and with a narrow size distribution of droplets. The generator preferably produces an aerosol at a rate of greater than about 0.5 liter per hour of droplets, more preferably greater than about 2 liters per hour of droplets, still more preferably greater than about 5 liters per hour of droplets, even more preferably greater than about 10 liters per hour of droplets and most preferably greater than about 40 liters per hour of droplets. For example, when the aerosol generator has a 400 transducer design, as described with reference to FIGS. 4–21, the aerosol generator is capable of producing a high quality aerosol having high droplet loading as previously described, at a total production rate of preferably greater than about 10 liters per hour of liquid feed, more preferably greater than about 15 liters per hour of liquid feed, even more preferably greater than about 20 liters per hour of liquid feed and most preferably greater than about 40 liters per hour of liquid feed.

Under most operating conditions, when using such an aerosol generator, total particulate product produced is preferably greater than about 0.5 gram per hour per transducer, more preferably greater than about 0.75 gram per hour per transducer, even more preferably greater than about 1.0 gram per hour per transducer and most preferably greater than about 2.0 grams per hour per transducer.

One significant aspect of the process of the present invention for manufacturing particulate materials is the unique flow characteristics encountered in the furnace relative to laboratory scale systems. The maximum Reynolds number attained for flow in the furnace 110 with the present invention is very high, typically in excess of 500, preferably in excess of 1,000 and more preferably in excess of 2,000. In most instances, however, the maximum Reynolds number for flow in the furnace will not exceed 10,000, and preferably will not exceed 5,000. This is significantly different from lab-scale systems where the Reynolds number for flow in a reactor is typically lower than 50 and rarely exceeds 100.

The Reynolds number is a dimensionless quantity characterizing flow of a fluid which, for flow through a circular cross sectional conduit is defined as:

$$Re = \frac{\rho v d}{\mu}$$

where: ρ=fluid density; v=fluid mean velocity; d=conduit inside diameter; and μ=fluid viscosity.

It should be noted that the values for density, velocity and viscosity will vary along the length of the furnace 110. The maximum Reynolds number in the furnace 110 is typically attained when the average stream temperature is at a maximum, because the gas velocity is at a very high value due to gas expansion when heated.

One problem with operating under flow conditions at a high Reynolds number is that undesirable volatilization of components is much more likely to occur than in systems having flow characteristics as found in laboratory-scale systems. The volatilization problem occurs with the present invention, because the furnace is typically operated over a substantial section of the heating zone in a constant wall heat flux mode, due to limitations in heat transfer capability. This is significantly different than operation of a furnace at a laboratory scale, which typically involves operation of most of the heating zone of the furnace in a uniform wall temperature mode, because the heating load is sufficiently small that the system is not heat transfer limited.

With the present invention, it is typically preferred to heat the aerosol stream in the heating zone of the furnace as quickly as possible to the desired temperature range for particle manufacture. Because of flow characteristics in the furnace and heat transfer limitations, during rapid heating of the aerosol the wall temperature of the furnace can significantly exceed the maximum average target temperature for the stream. This is a problem because, even though the average stream temperature may be within the range desired, the wall temperature may become so hot that components in the vicinity of the wall are subjected to temperatures high enough to undesirably volatilize the components. This volatilization near the wall of the furnace can cause formation of significant quantities of ultrafine particles that are outside of the size range desired.

Therefore, with the present invention, it is preferred that when the flow characteristics in the furnace are such that the Reynolds number through any part of the furnace exceeds 500, more preferably exceeds 1,000, and most preferably exceeds 2,000, the maximum wall temperature in the furnace should be kept at a temperature that is below the temperature at which a desired component of the final particles would exert a vapor pressure not exceeding about 200 millitorr, more preferably not exceeding about 100 millitorr, and most preferably not exceeding about 50 millitorr. Furthermore, the maximum wall temperature in the furnace should also be kept below a temperature at which an intermediate component, from which a final component is to be at least partially derived, should also have a vapor pressure not exceeding the magnitudes noted for components of the final product.

In addition to maintaining the furnace wall temperature below a level that could create volatilization problems, it is also important that this not be accomplished at the expense of the desired average stream temperature. The maximum average stream temperature must be maintained at a high enough level so that the particles will have a desired high density. The maximum average stream temperature should, however, generally be a temperature at which a component in the final particles, or an intermediate component from which a component in the final particles is at least partially derived, would exert a vapor pressure not exceeding about 100 millitorr, preferably not exceeding about 50 millitorr, and most preferably not exceeding about 25 millitorr.

So long as the maximum wall temperature and the average stream temperature are kept below the point at which detrimental volatilization occurs, it is generally desirable to heat the stream as fast as possible and to remove resulting particles from the furnace immediately after the maximum stream temperature is reached in the furnace. With the present invention, the average residence time in the heating zone of the furnace may typically be maintained at shorter than about 4 seconds, preferably shorter than about 2 seconds, more preferably shorter than about 1 second, still more preferably shorter than about 0.5 second, and most preferably shorter than about 0.2 second.

Another significant issue with respect to operating the process of the present invention, which includes high aerosol flow rates, is loss within the system of materials intended for incorporation into the final particulate product. Material losses in the system can be quite high if the system is not properly operated. If system losses are too high, the process would not be practical for use in the manufacture of particulate products of many materials. This has typically not been a major consideration with laboratory-scale systems.

One significant potential for loss with the process of the present invention is thermophoretic losses that occur when a hot aerosol stream is in the presence of a cooler surface. In that regard, the use of the quench cooler, as previously described, with the process of the present invention provides an efficient way to cool the particles without unreasonably high thermophoretic losses. There is also, however, significant potential for losses occurring near the end of the furnace and between the furnace and the cooling unit.

It has been found that thermophoretic losses in the back end of the furnace can be significantly controlled if the heating zone of the furnace is operated such that the maximum stream temperature is not attained until near the end of the heating zone in the furnace, and at least not until the last third of the heating zone. When the heating zone includes a plurality of heating sections, the maximum average stream temperature should ordinarily not occur until at least the last heating section. Furthermore, the heating zone should typically extend to as close to the exit of the furnace as possible. This is counter to conventional thought which is to typically maintain the exit portion of the furnace at a low temperature to avoid having to seal the furnace outlet at a high temperature. Such cooling of the exit portion of the furnace, however, significantly promotes thermophoretic losses. Furthermore, the potential for operating problems that could result in thermophoretic losses at the back end of the furnace are reduced with the very short residence times in the furnace for the present invention, as discussed previously.

Typically, it would be desirable to instantaneously cool the aerosol upon exiting the furnace. This is not possible. It is possible, however, to make the residence time between the furnace outlet and the cooling unit as short as possible. Furthermore, it is desirable to insulate the aerosol conduit occurring between the furnace exit and the cooling unit entrance. Even more preferred is to insulate that conduit and, even more preferably, to also heat that conduit so that the wall temperature of that conduit is at least as high as the average stream temperature of the aerosol stream. Furthermore, it is desirable that the cooling unit operate in a manner such that the aerosol is quickly cooled in a manner to prevent thermophoretic losses during cooling. The quench cooler, described previously, is very effective for cooling with low losses. Furthermore, to keep the potential for thermophoretic losses very low, it is preferred that the residence time of the aerosol stream between attaining the maximum stream temperature in the furnace and a point at which the aerosol has been cooled to an average stream temperature below about 200° C. is shorter than about 2 seconds, more preferably shorter than about 1 second, and even more preferably shorter than about 0.5 second and most preferably shorter than about 0.1 second. In most instances, the maximum average stream temperature attained in the furnace will be greater than about 800° C. Furthermore, the total residence time from the beginning of the heating zone in the furnace to a point at which the average stream temperature is at a temperature below about 200° C. should typically be shorter than about 5 seconds, preferably shorter than about 3 seconds, more preferably shorter than about 2 seconds, and most preferably shorter than about 1 second.

Another part of the process with significant potential for thermophoretic losses is after particle cooling until the particles are finally collected. Proper particle collection is very important to reducing losses within the system. The potential for thermophoretic losses is significant following particle cooling because the aerosol stream is still at an elevated temperature to prevent detrimental condensation of water in the aerosol stream. Therefore, cooler surfaces of particle collection equipment can result in significant thermophoretic losses.

To reduce the potential for thermophoretic losses before the particles are finally collected, it is important that the transition between the cooling unit and particle collection be as short as possible. Preferably, the output from the quench cooler is immediately sent to a particle separator, such as a filter unit or a cyclone. In that regard, the total residence time of the aerosol between attaining the maximum average stream temperature in the furnace and the final collection of the particles is preferably shorter than about 2 seconds, more preferably shorter than about 1 second, still more preferably shorter than about 0.5 second and most preferably shorter than about 0.1 second. Furthermore, the residence time between the beginning of the heating zone in the furnace and final collection of the particles is preferably shorter than about 6 seconds, more preferably shorter than about 3 seconds, even more preferably shorter than about 2 seconds, and most preferably shorter than about 1 second. Furthermore, the potential for thermophoretic losses may further be reduced by insulating the conduit section between the cooling unit and the particle collector and, even more preferably, by also insulating around the filter, when a filter is used for particle collection. The potential for losses may be reduced even further by heating of the conduit section between the cooling unit and the particle collection equipment, so that the internal equipment surfaces are at least slightly warmer than the aerosol stream average stream temperature. Furthermore, when a filter is used for particle collection, the filter could be heated. For example, insulation could be wrapped around a filter unit, with electric heating inside of the insulating layer to maintain the walls of the filter unit at a desired elevated temperature higher than the temperature of filter elements in the filter unit, thereby reducing thermophoretic particle losses to walls of the filter unit.

Even with careful operation to reduce thermophoretic losses, some losses will still occur. For example, some particles will inevitably be lost to walls of particle collection equipment, such as the walls of a cyclone or filter housing. One way to reduce these losses, and correspondingly increase product yield, is to periodically wash the interior of the particle collection equipment to remove particles adhering to the sides. In most cases, the wash fluid will be water, unless water would have a detrimental effect on one of the components of the particles. For example, the particle collection equipment could include parallel collection paths. One path could be used for active particle collection while the other is being washed. The wash could include an automatic or manual flush without disconnecting the equipment. Alternatively, the equipment to be washed could be disconnected to permit access to the interior of the equipment for a thorough wash. As an alternative to having parallel collection paths, the process could simply be shut down occasionally to permit disconnection of the equipment for washing. The removed equipment could be replaced with a clean piece of equipment and the process could then be resumed while the disconnected equipment is being washed.

For example, a cyclone or filter unit could periodically be disconnected and particles adhering to interior walls could be removed by a water wash. The particles could then be dried in a low temperature dryer, typically at a temperature of lower than about 50° C.

Another area for potential losses in the system, and for the occurrence of potential operating problems, is between the outlet of the aerosol generator and the inlet of the furnace. Losses here are not due to thermophoresis, but rather to liquid coming out of the aerosol and impinging and collecting on conduit and equipment surfaces. Although this loss is undesirable from a material yield standpoint, the loss may be even more detrimental to other aspects of the process. For example, water collecting on surfaces may release large droplets that can lead to large particles that detrimentally contaminate the particulate product. Furthermore, if accumulated liquid reaches the furnace, the liquid can cause excessive temperature gradients within the furnace tube, which can cause furnace tube failure, especially for ceramic tubes. One way to reduce the potential for undesirable liquid buildup in the system is to provide adequate drains. In that regard, it is preferred that a drain be placed as close as possible to the furnace inlet to prevent liquid accumulations from reaching the furnace. The drain should be placed, however, far enough in advance of the furnace inlet such that the stream temperature is lower than about 80° C. at the drain location.

Another way to reduce the potential for undesirable liquid buildup is for the conduit between the aerosol generator outlet and the furnace inlet to be of a substantially constant cross-sectional area and configuration. Preferably, the conduit beginning with the aerosol generator outlet, passing through the furnace and continuing to at least the cooling unit inlet is of a substantially constant cross-sectional area and geometry.

Another way to reduce the potential for undesirable buildup is to heat at least a portion, and preferably the entire length, of the conduit between the aerosol generator and the inlet to the furnace. For example, the conduit could be wrapped with a heating tape to maintain the inside walls of the conduit at a temperature higher than the temperature of the aerosol. The aerosol would then tend to concentrate toward the center of the conduit due to thermophoresis. Fewer aerosol droplets would, therefore, be likely to impinge on conduit walls or other surfaces making the transition to the furnace.

Figure 36:
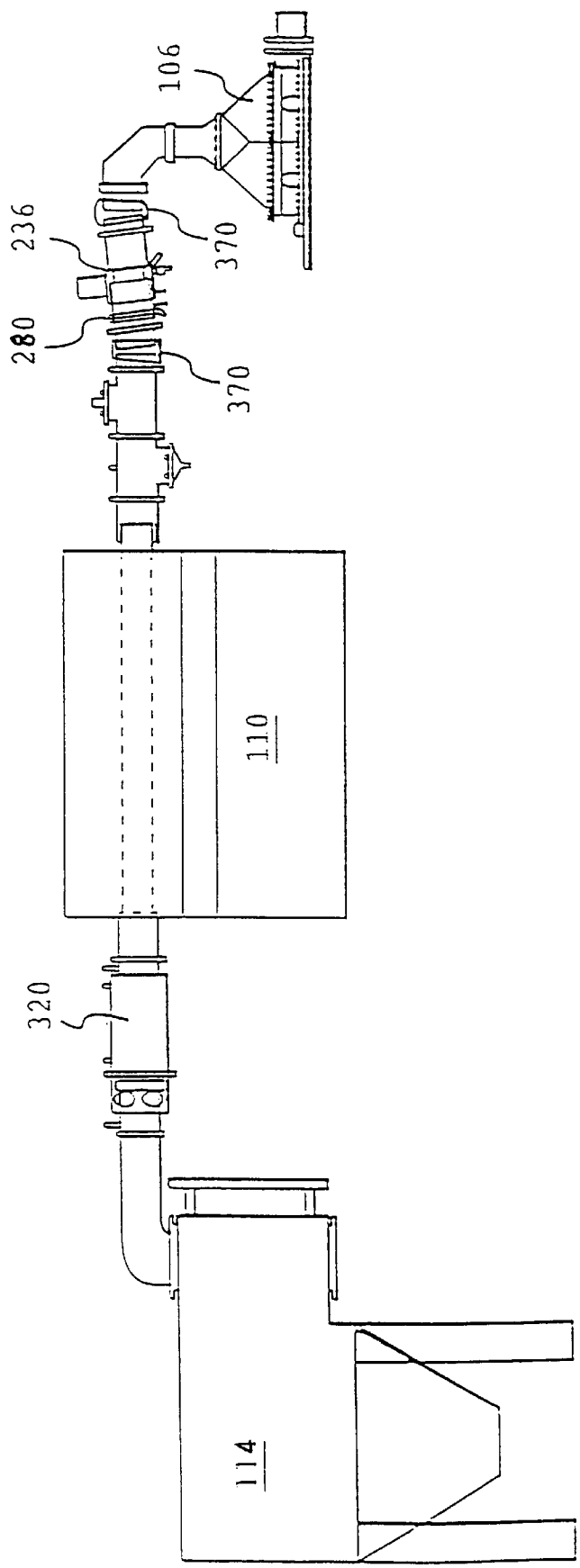

Another way to reduce the potential for undesirable liquid buildup is to introduce a dry gas into the aerosol between the aerosol generator and the furnace. Referring now to FIG. 36, one embodiment of the process is shown for adding a dry gas 118 to the aerosol 108 before the furnace 110. Addition of the dry gas 118 causes vaporization of at least a part of the moisture in the aerosol 108, and preferably substantially all of the moisture in the aerosol 108, to form a dried aerosol 119, which is then introduced into the furnace 110.

The dry gas 118 will most often be dry air, although in some instances it may be desirable to use dry nitrogen gas or some other dry gas. If sufficient a sufficient quantity of the dry gas 118 is used, the droplets of the aerosol 108 are substantially completely dried to beneficially form dried precursor particles in aerosol form for introduction into the furnace 110, where the precursor particles are then pyrolyzed to make a desired particulate product. Also, the use of the dry gas 118 typically will reduce the potential for contact between droplets of the aerosol and the conduit wall, especially in the critical area in the vicinity of the inlet to the furnace 110. In that regard, a preferred method for introducing the dry gas 118 into the aerosol 108 is from a radial direction into the aerosol 108. For example, equipment of substantially the same design as the quench cooler, described previously with reference to FIGS. 29–31, could be used, with the aerosol 108 flowing through the interior flow path of the apparatus and the dry gas 118 being introduced through perforated wall of the perforated conduit. An alternative to using the dry gas 118 to dry the aerosol 108 would be to use a low temperature thermal preheater/dryer prior to the furnace 110 to dry the aerosol 108 prior to introduction into the furnace 110. This alternative is not, however, preferred.

Still another way to reduce the potential for losses due to liquid accumulation is to operate the process with equipment configurations such that the aerosol stream flows in a vertical direction from the aerosol generator to and through the furnace. For smaller-size particles, those smaller than about 1.5 $\mu$m, this vertical flow should, preferably, be vertically upward. For larger-size particles, such as those larger than about 1.5 $\mu$m, the vertical flow is preferably vertically downward.

Furthermore, with the process of the present invention, the potential for system losses is significantly reduced because the total system retention time from the outlet of the generator until collection of the particles is preferably shorter than about 15 seconds, more preferably shorter than about 10 seconds, even more preferably shorter than about 7 seconds and most preferably shorter than about 5 seconds.

For the production of glass particles according to the present invention, the liquid feed 102 includes at least one metal oxide precursor for preparation of the glass particles 112. The metal oxide precursor may be a substance in either a liquid or solid phase of the liquid feed 102. Typically, the metal oxide precursor will be a metal-containing compound, such as a metal salt, dissolved in a liquid solvent of the liquid feed 102. The metal oxide precursor may undergo one or more chemical reactions in the furnace 110 to assist in production of the glass particles 112. Alternatively, the metal oxide precursor may contribute to formation of the glass particles 112 without undergoing chemical reaction. This could be the case, for example, when the liquid feed 102 includes suspended oxide particles as a precursor material, such as particulate silica.

The liquid feed 102 thus includes the chemical components that will form the glass particles 112. For example, the liquid feed 102 can comprise a solution containing nitrates, acetates, chlorides, sulfates, hydroxides, or oxalates of a metal. Particularly preferred precursor salts include metal nitrates and metal acetates. These salts are typically highly soluble in water and the solutions maintain a low viscosity. Metal nitrates are even more preferred since they do not contain any carbon that can potentially contaminate the end-product. It may be desirable to acidify the solution to increase the solubility, such as by adding hydrochloric acid.

The precursor solution can also include solid particulates, for example, the precursor solution can include particulate silica as a precursor for a silicate glass.

The solution preferably has a precursor concentration that is unsaturated to avoid the possibility of undesirable precipitate formation. The solution preferably includes a soluble precursor to yield a concentration of from about 1 to about 50 weight percent of the glass composition, more preferably from about 1 to 20 weight percent of the glass composition and even more preferably from about 3 to about 15 weight percent of the glass composition, such as about 5 to 7.5 weight percent of the glass composition. The final particle size of the glass particles 112 is also influenced by the precursor concentration. Generally, lower precursor concentrations will yield glass particles having a smaller average particle size.

Preferably, the solvent is aqueous-based for ease of operation, although other solvents, such as toluene, may be desirable. As is disclosed above, the pH of the aqueous-based solutions can be adjusted to alter the solubility characteristics of the precursor in the solution or the stability of, for example, colloid particles in the precursor solution. In addition to the foregoing, the liquid feed 102 may also include other additives that contribute to the formation of the particles.

Thus, the liquid feed 102 may include multiple precursor materials, which may be present together in a single phase or separately in multiple phases. For example, the liquid feed 102 may include multiple precursors in solution in a single liquid vehicle. Alternatively, one precursor material could be in a solid particulate phase and a second precursor material could be in a liquid phase. Also, one precursor material could be in one liquid phase and a second precursor material could be in a second liquid phase, such as could be the case for when the liquid feed 102 comprises an emulsion.

A carrier gas 104 under controlled pressure is introduced to the aerosol generator to move the droplets away from the generator. The carrier gas 104 may comprise any gaseous medium in which droplets produced from the liquid feed 102 may be dispersed in aerosol form. Also, the carrier gas 104 may be inert, in that the carrier gas 104 does not participate in formation of the particles 112. Alternatively, the carrier gas 104 may have one or more active components that contribute to formation of the particles 112. For the production of glass particles 112, the preferred carrier gas includes air since it is a low cost gas that can supply sufficient oxygen to form the glass particles.

The carrier gas 104 carries the aerosol through a heated reaction zone, as is discussed above. According to the present invention, the reaction temperature in the heating zone is preferably near the softening point of the glass composition to produce a dense material. To produce porous and/or hollow materials, the temperature is preferably below the glass transition temperature of the glass composition. Although the exact temperature can vary for different glass compositions, it is generally preferred that the reaction temperature is from about 300° C. to about 1500° C., and more preferably from about 500° C. to about 800° C. In most instances, it is preferred that the temperature be at least about 600° C. to ensure complete reaction of the particles.

Depending on the reaction temperature, the residence time in the heating zone can vary. It is preferred however that the residence time be at least about 2 seconds and typically no more than about 15 seconds. It is often preferred to adjust the process parameters to accommodate longer residence times at lower temperatures to ensure that volatile components such as PbO do not volatilize from the glass composition.

To form substantially uniform coatings on the surface of the glass particles, if desired, a reactive gas composition can be contacted with the glass particles at an elevated temperature after the particles have been formed. For example, the reactive gas can be introduced into the heated reaction zone at the distal end so that the desired compound, for example a metal, deposits on the surface of the particles.

More specifically, the droplets can enter the heated reaction zone at a first end such that the droplets move through the heating zone and form the glass particles. At the opposite end of the heating zone, a reactive gas composition can be introduced such that the reactive gas composition contacts the glass particles at an elevated temperature. Alternatively, the reactive gas composition can be contacted with the heated particles in a separate heating zone located downstream from the heated reaction zone.

Coatings can be generated on the particle surface by a number of different mechanisms. One or more precursors can vaporize and fuse to the hot particle surface and thermally react resulting in the formation of a thin-film coating by chemical vapor deposition (CVD). Preferred coatings deposited by CVD include elemental metals. Further, the coating can be formed by physical vapor deposition (PVD) wherein a coating material physically deposits on the surface of the particles. Preferred coatings deposited by PVD include organic materials and elemental metals. Alternatively, the gaseous precursor can react in the gas phase forming small particles, for example less than about 5 nanometers in size, which then diffuse to the larger particle surface and sinter onto the surface, thus forming a coating. This method is referred to as gas-to-particle conversion (GPC). Whether such coating reactions occur by CVD, PVD or GPC is dependent on the reactor conditions, such as temperature, precursor partial pressure, water partial pressure and the concentration of particles in the gas stream. Another possible surface coating method is surface conversion of the surface of the particles by reaction with a vapor phase reactant to convert the surface of the glass particles to a different material than that originally contained in the particles.

The coatings are preferably as thin as possible while maintaining conformity about particle such that the glass surface is not substantially exposed. For example, coatings can have an average thickness of not greater than about 200 nanometers, preferably not greater than about 100 nanometers, and more preferably not greater than about 50 nanometers. For most applications, the coating should have an average thickness of at least about 5 nanometers.

The structural modification that can occur in the particle modifier 360 may be any modification to the structure or morphology of the particles 112. For example, the particles 112 may be annealed in the particle modifier 360 to densify the particles 112 or to crystallize the glass particles 112 into a polycrystalline form. Also, the glass particles may be annealed for a sufficient time to redistribute different material phases within the particles 112 or to alter the thermal properties of the glass.

The present invention is directed to glass powder batches wherein the particles constituting the powder batch preferably have a spherical morphology. Advantageously, the powders can also have a small average particle size and a narrow particle size distribution. It is preferred that the powders are also substantially unagglomerated and have a high purity. The powders according to the present invention are useful for a number of applications including use in thick film pastes for microelectronic applications.

The glass powder batches according to the present invention include a commercially useful quantity of glass particles. The glass particles preferably include at least a first glass phase. The glass phase can include any glass composition and the particularly preferred glass composition will depend upon the application of the powder.

According to one embodiment, the glass particles preferably include at least about 80 weight percent glass, and depending upon the application, preferably include at least about 90 weight percent glass and even more preferably at least about 95 weight percent glass. In one preferred embodiment, the particles include at least about 99 weight percent glass, that is, not greater than about 1 weight percent of a crystalline phase.

Glass compositions can vary and include many components. The following description of preferred glasses is by way of example, and is not meant to limit the present invention to specific glasses. The most common types of glasses are oxide glasses, which can generally be categorized as: silicates, based on $SiO_2$, and including sub-groups such as aluminosilicates; borates, based on $B_2O_3$; phosphates, based on $P_2O_5$; and germanates, based on $GeO_2$. The foregoing oxides are commonly referred to as the glass-formers. The structure of the glass can be modified through the addition of intermediate oxides, such as $Al_2O_3$, $Bi_2O_3$ and PbO. At high concentrations, these intermediate oxides can also be considered glass-formers. Glass compositions can also be modified by the addition of one or more alkali (e.g., Li, Na, K, Rb, Cs) oxides and alkaline earth (e.g., Mg, Ca, Sr, Ba) oxides. Non-oxide glass compositions, such as halide glasses and chalcogenide glasses, are used for specific applications.

The present invention is particularly applicable to complex glass compositions, which are those glass compositions that include at least two components in non-trivial amounts, for example ternary and quaternary glass compositions.

The silicate-based glasses are the most common and are preferred according to the present invention. A particularly preferred glass for some microelectronic applications are the dielectric borosilicate glasses, comprising at least $SiO_2$ and $B_2O_3$, such as the lead borosilicate glasses that also include PbO. An example of such a complex dielectric glass is given in Table I.

TABLE I

Typical Dielectric Glass Composition

| Component | Range (wt. %) |
|---|---|
| PbO | 50–74 |
| $B_2O_3$ | 10–25 |
| $SiO_2$ | 8–26 |
| $Al_2O_3$ | 0–5 |
| CaO | 0–6 |
| MgO | 0–4 |
| $Na_2O$ | 0–5 |

The weight percent of the individual components of the glass detailed in Table I can be selected to alter the properties of the glass, such as the dielectric constant, thermal expansion coefficient, glass transition temperature and the like. Specific examples of borosilicate glasses which are useful for electronic applications include those disclosed in U.S. Pat. No. 4,613,560 by Dueber et al.; U.S. Pat. No. 5,032,478 by Nebe et al.; U.S. Pat. No. 5,032,490 by Nebe et al.; and U.S. Pat. No. 5,173,457 by Shorthouse. Each of the foregoing U.S. Patents disclosing borosilicate glass compositions is incorporated herein by reference in their entirety.

Also preferred according to an embodiment of the present invention are the aluminosilicate glasses which include at least $SiO_2$ and $Al_2O_3$. A typical composition for an aluminosilicate glass is listed in Table II.

TABLE II

Typical Aluminosilicate Glass Composition

| Component | Range (wt. %) |
|---|---|
| $SiO_2$ | 54–55 |
| CaO | 13–15 |
| BaO | 3–4 |
| $B_2O_3$ | 6–8 |
| $Al_2O_3$ | 20–22 |

A specific example of an aluminosilicate glass is disclosed in U.S. Pat. No. 4,598,037 by Felten. It will be appreciated by those skilled in the art that combinations of the foregoing glasses also occur in the art. For example, aluminoborosilicate glasses are known, as is disclosed in U.S. Pat. No. 4,820,661 by Nair and U.S. Pat. No. 5,173,457 by Shorthouse. Each of the foregoing U.S. Patents disclosing aluminosilicate and alumino borosilicate glasses are incorporated herein by reference in their entirety.

It is an advantage of the present invention that the glass composition within the particles is homogeneous and well mixed on the atomic level and has substantially no phase segregation of the different phases in the particle. Such a high degree of homogeneity in complex glasses is often not obtainable by traditional forming methods, such as sol-gel or liquid precipitation. However, it may be desirable for some applications that the particles consist of two or more distinct phases, and such a composition can also be formed according to the present invention.

Typically, the complex glass composition will be formed from a liquid solution which includes both a glass-former precursor (e.g. $SiO_2$) and a precursor for the intermediate oxides and/or glass modifiers. The weight percentage of the different components can be adjusted by changing the relative ratios of precursors in the liquid precursor solution.

The glass powders according to one embodiment of the present invention include glass particles having a small average particle size. Although the preferred average size of the particles will vary according to the particular application of the powder, the weight average particle size of the particles is at least about 0.05 μm, preferably is at least about 0.1 μm and more preferably is at least about 0.3 μm. Further, according to this embodiment, the average particle size is preferably not greater than about 10 μm. More preferably the weight average particle size is not greater than about 5 μm, particularly not greater than about 3 μm.

Although such small average particle sizes are preferred for some applications, the present invention is also applicable to glass powders having a larger average particle size, such as up to about 20 μm. Such glass powders can advantageously be produced according to the present invention using, for example, a nozzle-type atomizer to produce an aerosol stream with increased aerosol droplet size.

According to a preferred embodiment of the present invention, the powder batch of glass particles has a narrow particle size distribution, such that the majority of glass particles are about the same size. Preferably, at least about 80 weight percent and more preferably at least about 90 weight percent of the particles are not larger than twice the weight average particle size. Thus, when the average particle size is about 2 μm, it is preferred that at least about 80 weight percent of the particles are not larger than 4 μm. Further, it is preferred that at least about 80 weight percent of the particles are not larger than about 1.5 times the weight average particle size. In a more preferred embodiment, at least about 90 weight percent of the particles are not larger than 1.5 times the average particle size. Thus, when the average particle size is about 2 μm, it is preferred that at least about 80 weight percent of the particles are not larger than 3 μm.

It is also possible according to the present invention to provide a glass powder batch having a bimodal particle size distribution. That is, the powder batch can include particles having two distinct and different average particle sizes. A bimodal particle size distribution can enhance the packing efficiency of the powder.

The glass powders produced by the processes described herein, namely spray pyrolysis, can form soft agglomerates as a result of their relatively high surface energy (compared to larger particles). It is also known to those skilled in the art that soft agglomerates may be dispersed easily by treatments such as exposure to ultrasound in a liquid medium or sieving. The particle size distributions described herein are measured by mixing samples of the powders in a medium such as water with a surfactant and a short exposure to ultrasound through either an ultrasonic bath or horn. The ultrasonic treatment supplies sufficient energy to disperse the soft agglomerates into primary spherical particles. The primary particle size distribution is then measured by light scattering in a Microtrac instrument. This provides a good measure of the useful dispersion characteristics of the powder because this simulates the dispersion of the particles in a liquid medium such as a paste or slurry that is used to deposit the particles in a device. Thus, the references to particle size herein refer to the primary particle size, such as after lightly dispersing the soft agglomerates of the powder.

The glass particles produced according to the present invention also have a high degree of purity and it is preferred that the particles include not greater than about 0.1 atomic percent impurities and more preferably not greater than about 0.01 atomic percent impurities. Since no milling of the particles is required to achieve small average particle sizes, there are substantially no undesired impurities such as alumina, zirconia or high carbon steel in the powder batch. According to one preferred embodiment, the glass particles include less than about 100 ppm, more preferably less than 50 ppm, of metallic impurities that can discolor the glass, such as chromium.

The formation of hollow particles is common in spray pyrolysis. In the present invention, it has been found that the formation of hollow particles can be controlled through the selection of precursors, precursor concentration, pyrolysis temperature and residence time. According to one embodiment of the present invention, the glass particles are dense (e.g. not hollow or porous), as measured by helium pycnometry. According to this embodiment, the glass particles have a particle density of at least about 80% of the theoretical value, more preferably at least about 90% of the theoretical value and even more preferably at least about 95% of the theoretical value. In one embodiment, the particle density is at least about 99% of the theoretical value. The theoretical density can be easily calculated for glasses based on the relative percentages of each component. High density particles provide many advantages over porous particles, including reduced shrinkage during sintering and improved flow properties.

According to another embodiment, however, the glass particles are hollow spheres having a reduced density. As is discussed above, such hollow particles can be produced, for example, by reducing the reaction temperature during manufacture to below the glass transition temperature (Tg) of the glass. Hollow particles can also be produced by careful selection of the precursors. Such hollow particles are useful in electronic applications requiring a low dielectric constant, such as a dielectric constant of less than about 2.

The glass particles according to a preferred embodiment of the present invention are also substantially spherical in shape. That is, the particles are not jagged or irregular in shape. Spherical particles are particularly advantageous because they are able to disperse more readily in a paste or other liquid medium and impart advantageous flow characteristics to compositions containing the particles.

In addition, the glass powder according to the present invention has a low surface area. The particles are substantially spherical, which reduces the total surface area for a given mass of powder. Further, the elimination of larger particles from the powder batch eliminates the porosity that is typically associated with open pores on the surface of such larger particles. Due to the elimination of the larger particles, the powder advantageously has a lower surface area. Surface area is typically measured using the BET nitrogen adsorption method which is indicative of the surface area of the powder, including the surface area of accessible pores on the surface of the particles. For a given particle size distribution, a lower value of surface area per unit mass of powder generally indicates solid or non-porous particles. The reactivity of powders having a low surface area is reduced. This characteristic can advantageously extend the shelf life of such powders. Preferably, the glass powders have a surface area that is close, such as within about 5 percent, of the calculated geometric surface area which is calculated for monodispersed spheres having the same average particle size as the glass powder.

In addition, the powder batches of glass particles according to the present invention are substantially unagglomerated, that is, they include substantially no hard agglomerates of the glass particles. Hard agglomerates are physically coalesced lumps of two or more particles that behave as one large particle. Hard agglomerates are disadvantageous in most applications, particularly when the glass powder is applied to a substrate in a liquid vehicle, such as a thick film paste. It is preferred that no more than about 1.0 weight percent of the glass particles in the powder batch of the present invention are in the form of hard agglomerates. More preferably, no more than about 0.5 weight percent of the particles are in the form of hard agglomerates. In the event that hard agglomerates do form, they can optionally be broken up, such as by jet-milling the powder.

According to one embodiment of the present invention, the glass particles are composite glass particles, wherein the individual particles include at least a first glass phase and at least a second phase associated with the glass phase. The second phase can be, for example, a metal. Preferred metals are the noble metals such as gold or silver. Such composites can be produced by adding a salt of the metal to the precursor solution, such as silver nitrate.

According to another embodiment of the present invention, the glass particles are coated particles that include a particulate coating or non-particulate (film) coating that substantially encapsulates the outer surface of the particles. Preferably, the coating is very thin and has an average thickness of not greater than about 200 nanometers, more preferably not greater than about 100 nanometers, and even more preferably not greater than about 50 nanometers. While the coating is thin, the coating should substantially encapsulate the entire particle such that substantially no glass surface is exposed. Accordingly, the coating preferably has an average thickness of at least about 5 nanometers.

The coating can be a metal or other inorganic compound, or can be an organic compound. For example, the particles can be coated with a metal to utilize the surface properties of the metal coating. The particles can include more than one coating, if multiple coatings are desirable.

Further, a dielectric coating, either organic or inorganic, can be used to achieve the appropriate surface charge characteristics to carry out deposition processes such as electrostatic deposition, discussed hereinbelow.

The glass particles of the present invention can advantageously be coated with an organic compound, for example a surfactant to provide improved dispersion which will result in smoother prints having lower lump counts when applied as a paste. The organic compound for coating the particles can be selected from organic compounds such as PMMA (polymethylmethacrylate), polystyrene or the like. The organic coating preferably has an average thickness of not greater than about 100 nanometers, and more preferably not greater than about 50 nanometers. The organic coating is substantially dense and continuous about the particle.

The coating can also be comprised of one or more monolayer coatings, such as from about 1 to 3 monolayer coatings. A monolayer coating is formed by the reaction of an organic or an inorganic molecule with the surface of the particles to form a coating layer that is essentially one molecular layer thick. In particular, the formation of a monolayer coating by reaction of the surface of the particle with a functionalized organo silane such as halo- or amino-silanes, for example hexamethyldisilazane or trimethylsilylchloride, can be used to modify the hydrophobicity and hydrophilicity of the powders. Such coatings allow for greater control over the dispersion characteristics of the powder in a wide variety of paste compositions.

The monolayer coatings can also be applied to glass powders that have already been coated with an organic or inorganic coating thus providing better control over the corrosion characteristics (through the use of the thicker coating) as well as dispersibility (through the monolayer coating) of the particles.

The glass powder batches according to the present invention are useful in a number of applications and can be used to fabricate a number of novel devices and intermediate products. Such devices and intermediate products are included within the scope of the present invention.

The glass powders according to the present invention are particularly useful in microelectronic applications, including data processing applications and advanced display applications. Complex glasses, particularly borosilicate glasses, are commonly used as dielectric materials in microelectronic circuits. For such applications, the glass should have a low dielectric constant, good thermal expansion match to the substrate, a well controlled glass transition temperature ($T_g$) and low dielectric loss.

Glass powders can be deposited onto device surfaces or substrates by a number of different deposition methods which involve the direct deposition of the dry powder such as dusting, electrophotographic or electrostatic precipitation, while other deposition methods involve liquid vehicles such as ink jet printing, liquid delivery from a syringe, micropens, toner, slurry deposition, paste-based methods and electrophoresis. In all these deposition methods, the powders described in the present invention show a number of distinct advantages over powders produced by other methods. For example, small, spherical, narrow size distribution glass particles are more easily dispersed in liquid vehicles, they remain dispersed for a longer period and allow printing of smoother and finer features compared to powder made by alternative methods.

Some glasses are also used in metal thick-film paste compositions to control the shrinkage of the paste during sintering and facilitate the bonding of the paste to the substrate. Generally, the glass should have good electrical resistivity, thermal shock resistance, good mechanical strength, good dielectric strength and low dielectric loss.

In the thick-film paste process, a viscous paste that includes a functional particulate phase (e.g. a metal powder and/or a dielectric glass) is screen printed onto a substrate. More particularly, a porous screen fabricated from stainless steel, polyester, nylon or similar inert material is stretched and attached to a rigid frame. A predetermined pattern is formed on the screen corresponding to the pattern to be printed. For example, a UV sensitive emulsion can be applied to the screen and exposed through a positive or negative image of the design pattern. The screen is then developed to remove portions of the emulsion in the pattern regions.

The screen is then affixed to a screen printing device and the thick film paste is deposited on top of the screen. The substrate to be printed is then positioned beneath the screen and the paste is forced through the screen and onto the substrate by a squeegee that traverses the screen. Thus, a pattern of traces and/or pads of the paste material is transferred to the substrate. The substrate with the paste applied in a predetermined pattern is then subjected to a drying and firing treatment to solidify and adhere the paste to the substrate.

Thick film pastes have a complex chemistry and generally include a functional phase, a binder phase and an organic vehicle phase. The functional phase include metal powders which provide conductivity. The binder phase can be, for example, a mixture of metal oxide or glass frit powders such as those according to the present invention. PbO based glasses are commonly used as binders. The function of the binder phase is to control the sintering of the film and assist the adhesion of the functional phase to the substrate and/or assist in the sintering of the functional phase. Reactive compounds can also be included in the paste to promote adherence of the functional phase to the substrate.

Thick film pastes also include an organic vehicle phase that is a mixture of solvents, polymers, resins and other organics whose main function is to provide the appropriate rheology (flow properties) to the paste. The liquid solvent assists in mixing of the components into a homogenous paste and substantially evaporates upon application of the paste to the substrate. Usually the solvent is a volatile liquid such as methanol, ethanol, terpineol, butyl carbitol, butyl carbitol acetate, aliphatic alcohols, esters, acetone and the like. The other organic vehicle components can include thickeners (sometimes referred to as organic binders), stabilizing agents, surfactants, wetting agents and the like. Thickeners provide sufficient viscosity to the paste and also acts as a binding agent in the unfired state. Examples of thickeners include ethyl cellulose, polyvinyl acetates, resins such as acrylic resin, cellulose resin, polyester, polyamide and the like. The stabilizing agents reduce oxidation and degradation, stabilize the viscosity or buffer the pH of the paste. For example, triethanolamine is a common stabilizer. Wetting agents and surfactants are well known in the thick film paste art and can include triethanolamine and phosphate esters.

The different components of the thick film paste are mixed in the desired proportions in order to produce a substantially homogenous blend wherein the functional phase is well dispersed throughout the paste. Typically, the thick film paste will include from about 5 to about 95 weight percent such as from about 60 to 85 weight percent, of the functional phase.

Examples of thick film pastes are disclosed in U.S. Pat. Nos. 4,172,733; 3,803,708; 4,140,817; and 3,816,097 all of which are incorporated herein by reference in their entirety.

Some applications of thick film pastes require higher tolerances than can be achieved using standard thick-film technology, as is described above. As a result, some thick film pastes have photo-imaging capability to enable the formation of lines and traces with decreased width and pitch. In this type of process, a photoactive thick film paste is applied to a substrate substantially as is described above. The paste can include, for example, a liquid vehicle such as polyvinyl alcohol, that is not cross-linked. The paste is then dried and exposed to ultraviolet light through a photomask to polymerize the exposed portions of paste and the paste is developed to remove unwanted portions of the paste. This technology permits higher density lines and other features to be formed. The combination of the foregoing technology with the glass powders of the present invention permits the fabrication of devices with resolution and tolerances as compared to conventional technologies using conventional glass powders.

In addition, a laser can be used instead of ultraviolet light through a mask. The laser can be scanned over the surface in a pattern thereby replacing the need for a mask. The laser light is of sufficiently low intensity that it does not heating the glass or polymer above its softening point. The unirradiated regions of the paste can be removed leaving a pattern.

Likewise, conventional paste technology utilizes heating of a substrate to remove the vehicle from a paste and to fuse particles together or modify them in some other way. A laser can be used to locally heat the paste layer and scanned over the paste layer thereby forming a pattern. The laser heating is confined to the paste layer and drives out the paste vehicle and heats the powder in the paste without appreciably heating the substrate. This allows heating of particles, delivered using pastes, without damaging a glass or even polymeric substrate.

Powders for use in thick-film pastes should have good dispersibility and flow properties. As is discussed above, the glass powders according to the present invention are substantially spherical in shape and are substantially unagglomerated. Due to this unique combination of properties, the powders disperse and flow in a thick-film paste better than conventional powders which are not spherical and contain agglomerates.

Other deposition methods for the powders can also be used. For example, a slurry method can be used to deposit the powder. The powder is typically dispersed in an aqueous slurry including reagents such as potassium silicate and polyvinyl alcohol, which aids in the adhesion of the powder to the surface. For example, the slurry can be poured onto the substrate and left to settle to the surface. After the powder has sedimented onto the substrate the supernatant liquid is decanted off and the powder layer is left to dry.

Glass particles can also be deposited electrophoretically or electrostatically. The particles are charged and are brought into contact with the substrate surface having localized portions of opposite charge. The layer is typically lacquered to adhere the particles to the substrate. Shadow masks can be used to produce the desired pattern on the substrate surface.

Ink-jet printing is another method for depositing the glass powders in a predetermined pattern. The powder is dispersed in a liquid medium and dispensed onto a substrate using an ink jet printing head that is computer controlled to produce a pattern. The glass powders of the present invention having a small size, narrow size distribution and spherical morphology can be printed into a pattern having a high density and high resolution. Other deposition methods utilizing a glass powder dispersed in a liquid medium include micro-pen or syringe deposition, wherein the powders are dispersed and applied to a substrate using a pen or syringe and are then allowed to dry.

Patterns can also be formed by using an ink jet or micropen (small syringe) to dispense sticky material onto a surface in a pattern. Powder is then transferred to the sticky regions. This transfer can be done is several ways. A sheet covered with powder can be applied to the surface with the sticky pattern. The powder sticks to the sticky pattern and does not stick to the rest of the surface. A nozzle can be used to transfer powder directly to the sticky regions.

Many methods for directly depositing materials onto surfaces require heating of the particles once deposited to sinter them together and densify the layer. The densification can be assisted by including a molecular precursor to a material in the liquid containing the particles. The particle/molecular precursor mixture can be directly written onto the surface using ink jet, micropen, and other liquid dispensing methods. This can be followed by heating in a furnace or heating using a localized energy source such as a laser. The heating converts the molecular precursor into the functional material contained in the particles thereby filling in the space between the particles with functional material.

Thus, the glass powders produced according to the present invention result in smoother powder layers when deposited by such liquid or dry powder based deposition methods. Smoother powder layers are the result of the smaller average particle size, spherical particle morphology and narrower particle size distribution compared to powders produced by other methods.

The glass powders of the present invention can also be used in resistor and/or thermistor component applications. For these applications, the glass powder is mixed with a conductive powder (e.g., a metal) in a specified ratio to control the resistance of the component. For these applications, the resistivity and temperature coefficient of resistance (TCR) for the glass must be well-controlled. A common problem in traditional pastes for these applications is segregation of the metal and glass powders due to the large difference in particle size between the two powders. The glass powder typically has an average size much greater than the average size of the metal powder. The glass powders of the present invention can advantageously have a size that is tailored to be similar to the size of the metal powder, e.g. less than about 5 $\mu$m, resulting in a more uniform paste and improved component properties. Glasses commonly used in thick-film paste applications include borosilicate glasses containing different amounts of modifiers such as $Al_2O_3$, $Bi_2O_3$, PbO, CdO, ZnO, BaO and CaO.

Structural applications of the glass powders according to the present invention include use as spacers for glass faceplates in display applications. The high tolerance of this application demands glass powders with well-controlled physical properties such as a small particle size and narrow size distribution.

One preferred application of the glass powders of the present invention is for the barrier ribs in a flat panel display, such as a plasma display panel. Such barrier ribs provide electrical insulation and must have well-controlled dielectric properties. Further, the ribs are narrow and have tightly controlled spacing in the device, therefore the powders must have well-controlled physical properties such as a small size and a narrow size distribution. The particles should also have a high purity so that the ribs are substantially transparent and do not discolor the viewing screen.

Other uses of glass powders can include high temperature/high pressure lubrication, such as for metal stamping. Glass powders are also used as sealants wherein the glass (referred to as a solder glass) is selected to have a lower softening point than the substrate glass. For example, a solder glass can be used to seal two glass plates together in liquid-crystal displays (LCD's). Other uses of the glass powders include dental applications, such as for crown and filling material wherein the glass is admixed with a ceramic and/or a resin. Glass powders in the form of beads or hollow micro spheres can also be used to deliver drugs or radiation into the body.

EXAMPLES

A complex glass precursor solution was prepared including colloidal particulate silica, boric acid, lead acetate, zinc acetate and aluminum nitrate. The solution was atomized using ultrasonic transducers at a frequency of about 1.6 MHZ to produce an aerosol of precursor droplets. Air was used as a carrier gas to move the aerosol through an elongated tubular furnace such that the droplets/particles had a residence time of about 10–12 seconds in the furnace.

The reaction temperature was varied to determine the effect of the reaction temperature on the formation of the particles. Reaction temperatures were 500° C., 600° C., 650° C. and 700° C. At 500° C. and 600° C., it was observed that the powder had a slightly tan color, indicating the presence of unreacted carbon from the acetate precursor. At 650° C. and 700° C., the powders were white. In all cases, the powders were spherical and unagglomerated.

In a further set of experiments, the same precursor solutions (colloidal silica, boric acid, lead acetate, zinc acetate and aluminum nitrate) at a total precursor concentration of 7.5 weight percent based on the glass composition were formed into an aerosol using a 7×7 array of ultrasonic transducers at a frequency of about 1.6 MHZ. A tubular furnace (36"×5.5" diameter) was used to heat the aerosol to the reaction temperature. The total residence time was about 2–3 seconds. Temperatures ranged from 400° C. to 1000° C. However, a fully reacted white powder was not obtainable. The color of the powder ranged from tan at lower temperatures to bright yellow at higher temperatures. It is believed that the residence time of 2–3 seconds was too short for the reaction of the acetates and complete elimination of carbon.

As a result, a precursor solution of nitrate precursors in distilled water was formed. The precursor solution included colloidal silica (Cabot HS-5, Cabot Corporation, MA), aluminum nitrate, boric acid, lead nitrate and zinc nitrate. The precursor solution was formed into an aerosol using ultrasonic transducers at a frequency of about 1.6 MHZ. Air was used as a carrier gas at a flow rates of about 4 CFM in a 72 inch by 5.5 inch heated tube, to yield residence times of about 4.5 seconds. The temperature of the furnace was experimentally varied at temperatures of 600° C., 650° C. and 700° C.

Figure 37:
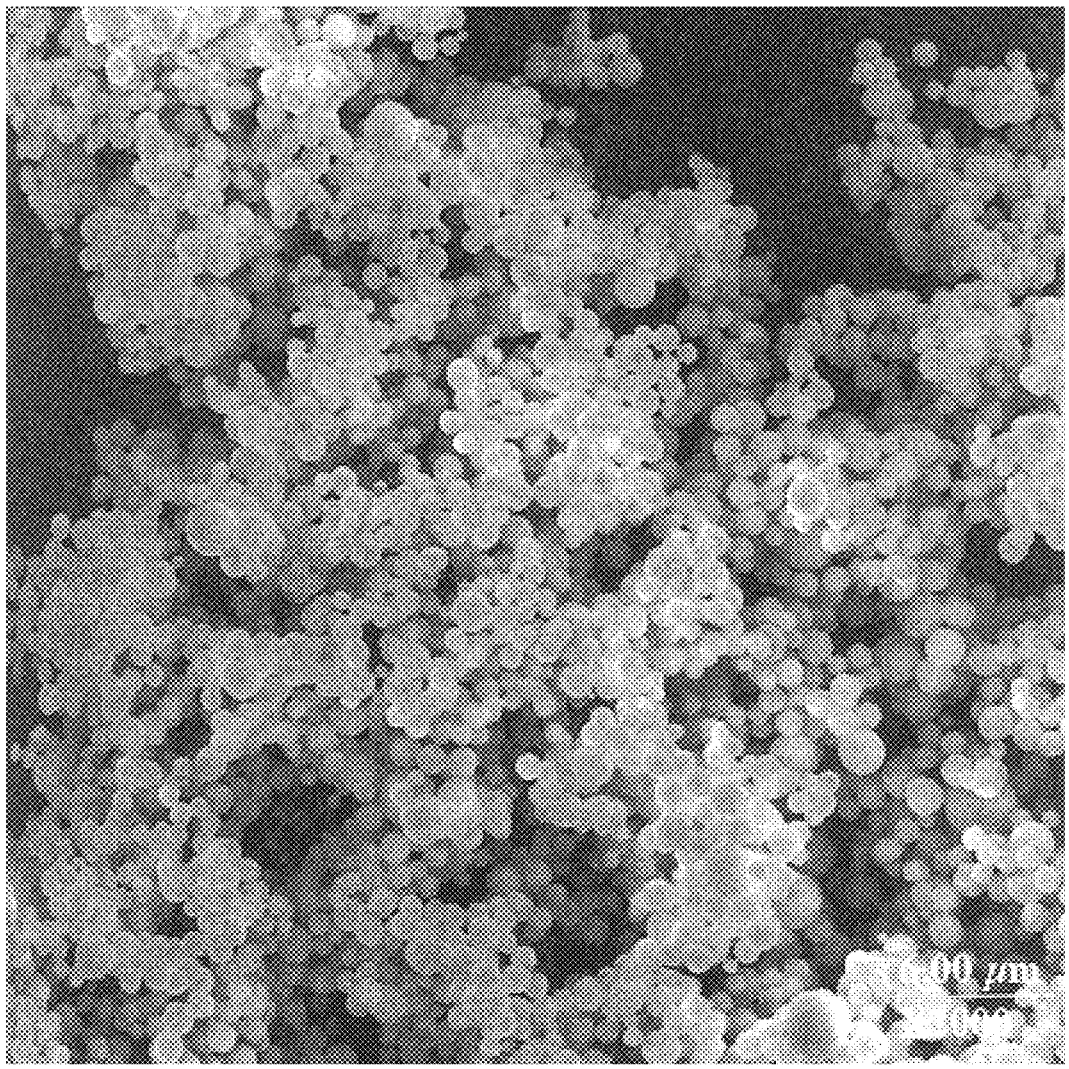
Figure 38:
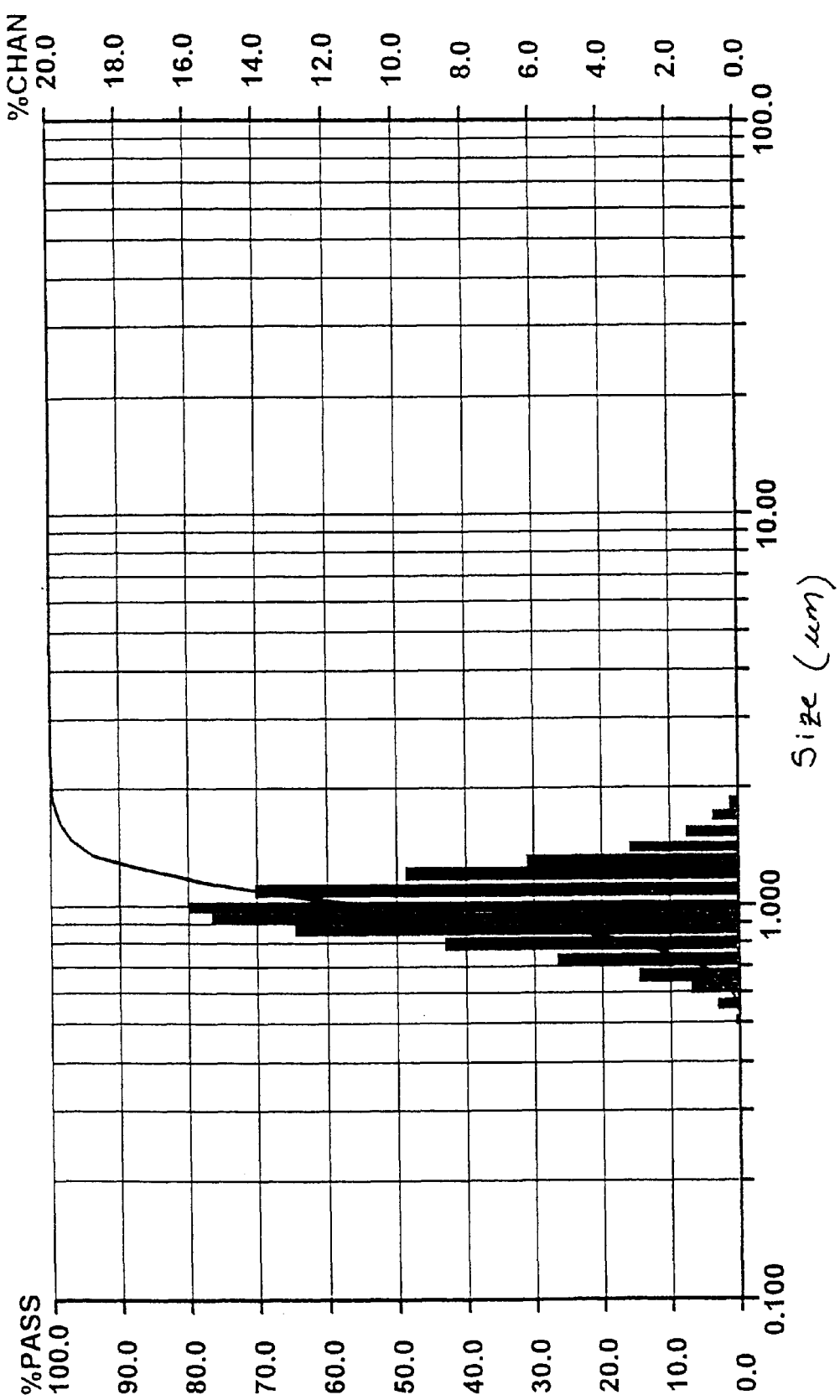

At the lower temperatures, below 600° C., the powder was non-spherical and angular, indicating unreacted nitrates were present. This was confirmed by x-ray diffraction. However, at 700° C. and a flow rate of 4 CFM, the particles were fully reacted and spherical. This complex glass powder is illustrated in FIG. 37 and the particles are spherical and unagglomerated. The particle size distribution is illustrated in FIG. 38 for particles which were collected in a cyclone, which further narrowed the size distribution of the powder. The volume average particle size of the powder was about 1 µm and there were substantially no particles greater than 2 µm. 90 percent of the particles had a size of less than 1.3 µm, and 90 percent of the particles were at least 0.74 µm.

Thus, it is believed that nitrate precursors are preferred over acetate precursors. The residence time of the aerosol should be sufficient to enable complete reaction of the precursors at a given temperature. Since some glass components, such as PbO, are highly volatile at high temperatures, it is preferred to heat the aerosol at low temperatures for longer residence times.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method for the production of glass particles, comprising the steps of:
    a) generating an aerosol of droplets from a liquid wherein said liquid is an aqueous-based liquid comprising at least a first glass precursor;
    b) moving said droplets in a carrier gas;
    c) pyrolyzing said droplets in an elongated tubular furnace at a reaction temperature of from about 500° C. to about 800° C. and for a residence time sufficient to remove liquid therefrom and convert said precursor to form glass particles; and
    d) collecting said glass particles in a particle collector.

2. A method as recited in claim 1, wherein said step of generating an aerosol comprises the step of ultrasonically atomizing said liquid.

3. A method as recited in claim 1, wherein said step of generating an aerosol comprises the step of generating said aerosol with an atomizing nozzle.

4. A method as recited in claim 1, wherein said carrier gas comprises air.

5. A method as recited in claim 1, where said pyrolyzing step comprises passing said droplets through a heating zone having a reaction temperature of at least about 600° C.

6. A method as recited in claim 1, wherein said glass particles comprise not greater than 0.1 atomic percent impurities.

7. A method as recited in claim 1, wherein said glass particles have a particle density of at least about 90° percent of the theoretical density.

8. A method as recited in claim 1, wherein said droplets in said aeorosol have a size distribution such that no greater than about 20 weight percent of the droplets in said aerosol are larger than about twice the weight average droplet size.

9. A method as recited in claim 1, wherein said liquid is a solution comprising at least one precursor selected from the group consisting of metal nitrates and metal acetates.

10. A method as recited in claim 1, wherein said liquid is a solution comprising metal nitrate precursors.

11. A method as recited in claim 1, wherein said liquid comprises at least a first particulate precursor.

12. A method as recited in claim 1, wherein said liquid comprises at least a first particulate precursor selected from the group consisting of silica and alumina.

13. A method as recited in claim 1, wherein said liquid comprises a particulate precursor having an average particle size of not greater than about 100 nm.

14. A method as recited in claim 1, wherein said liquid comprises at least two metal oxide precursors and wherein said glass is a complex glass.

15. A method as recited in claim 1, wherein said liquid comprises a particulate precursor that does not undergo substantial chemical reaction in said furnace and wherein said glass particles are glass composite particles.

16. A method as recited in claim 1, wherein said liquid comprises a metal precursor and wherein said glass particles are composite particles comprising a glass phase and a metallic phase.

17. A method as recited in claim 1, wherein said liquid comprises at least three metal oxide precursors and wherein said glass is a complex glass comprising at least three components.

18. A method as recited in claim 1, wherein said step of collecting said glass particles comprises collecting said glass particles using a cyclone separator.

19. A method as recited in claim 1, wherein said method further comprises the step of annealing said glass particles.

20. A method as recited in claim 1, wherein said method further comprises the step of coating said glass particles.

* * * * *

UNITED STATES PATENT AND TRADEMARK OFFICE
CERTIFICATE OF CORRECTION

PATENT NO. : 6,360,562 B1 Page 1 of 1
DATED : March 26, 2002
INVENTOR(S) : Kodas et al.

It is certified that error appears in the above-identified patent and that said Letters Patent is hereby corrected as shown below:

Column 38,
Line 32, please delete the word "aeorosol", and insert therefor -- aerosol --.

Signed and Sealed this

Eleventh Day of June, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.       : 6,360,562 B1                                       Page 1 of 1
APPLICATION NO.  : 09/141394
DATED            : March 26, 2002
INVENTOR(S)      : Hampden-Smith et al.

It is certified that error appears in the above-identified patent and that said Letters Patent is hereby corrected as shown below:

Column 1
Line 9, insert the following paragraph:

--STATEMENT REGARDING FEDERALLY-SPONSORED RESEARCH/ DEVELOPMENT
This invention was made with Government support under contracts N00014-95-C-0278 and N00014-96-C-0395 awarded by the Office of Naval Research. The Government has certain rights in the invention.--

Signed and Sealed this

Fifth Day of September, 2006

JON W. DUDAS
*Director of the United States Patent and Trademark Office*